United States Patent
Matsuda

(10) Patent No.: US 11,363,962 B2
(45) Date of Patent: Jun. 21, 2022

(54) ELECTRO-MAGNET DEVICE FOR MAGNETIC PARTICLE IMAGING AND MAGNETIC PARTICLE IMAGING DEVICE

(71) Applicant: Mitsubishi Electric Corporation, Tokyo (JP)

(72) Inventor: Tetsuya Matsuda, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 71 days.

(21) Appl. No.: 17/042,941

(22) PCT Filed: Mar. 5, 2019

(86) PCT No.: PCT/JP2019/008489
§ 371 (c)(1),
(2) Date: Sep. 29, 2020

(87) PCT Pub. No.: WO2019/225111
PCT Pub. Date: Nov. 28, 2019

(65) Prior Publication Data
US 2021/0015396 A1    Jan. 21, 2021

(30) Foreign Application Priority Data
May 21, 2018  (JP) .............................. JP2018-097384

(51) Int. Cl.
*A61B 5/0515* (2021.01)
*G01R 33/12* (2006.01)
(Continued)

(52) U.S. Cl.
CPC ........ *A61B 5/0515* (2013.01); *G01R 33/1276* (2013.01); *H01F 7/064* (2013.01); *H01F 7/202* (2013.01); *A61B 2562/0223* (2013.01)

(58) Field of Classification Search
CPC .......... A61B 5/0515; A61B 2562/0223; G01R 33/1276; H01F 7/064; H01F 7/202
See application file for complete search history.

(56) References Cited

U.S. PATENT DOCUMENTS

| 8,350,566 B2 | 1/2013 | Ohyu et al. |
| 9,044,160 B2 | 6/2015 | Knopp et al. |

(Continued)

FOREIGN PATENT DOCUMENTS

| JP | 2008-307254 A | 12/2008 |
| JP | 2009-56232 A  | 3/2009 |

(Continued)

OTHER PUBLICATIONS

International Search Report and Written Opinion dated Jun. 11, 2019 for PCT/JP2019/008489 filed on Mar. 5, 2019, 7 pages including English Translation of the International Search Report.

(Continued)

*Primary Examiner* — Gregory H Curran
(74) *Attorney, Agent, or Firm* — Xsensus LLP

(57) ABSTRACT

Provided is an electromagnetic device for magnetic particle imaging, including: a return yoke having a gap, which extends in a Y direction and forms a magnetic field space; a gradient magnetic field generating unit, which is provided to the return yoke, and is configured to generate, in the magnetic field space, a gradient magnetic field in an X direction, and to form, in the magnetic field space, a zero-field region extending in the Y direction; an alternating magnetic field generating unit, which is provided to the return yoke, and is configured to generate an alternating magnetic field in the magnetic field space; and a rotation mechanism configured to rotate the gradient magnetic field and the alternating magnetic field relative to a subject with a Z direction being a rotation axis.

16 Claims, 28 Drawing Sheets

(51) Int. Cl.
*H01F 7/06* (2006.01)
*H01F 7/20* (2006.01)

(56) References Cited

U.S. PATENT DOCUMENTS

| 10,215,826 B2 * | 2/2019 | Heinen | G01R 33/10 |
| 2015/0008910 A1 * | 1/2015 | Goodwill | G01R 33/0213 |
|  |  |  | 324/228 |
| 2018/0017641 A1 * | 1/2018 | Goodwill | G01R 33/1276 |

FOREIGN PATENT DOCUMENTS

| JP | 2010-088683 A | 4/2010 |
| JP | 2013-502262 A | 1/2013 |

OTHER PUBLICATIONS

Notice of Reasons for Refusal issued in corresponding JP Application No. 2020-521041, dated Feb. 9, 2021, 13 pages, with English Translation.
Erica E. Mason et al., Design Analysis of an MPI Human Functional Brain Scanner, International Journal on Magnetic Particle Imaging, Infinite Science Publishing, (published online Mar. 23, 2017) vol. 3, No. 1, 12 pages.

* cited by examiner

ELECTRO-MAGNET DEVICE FOR MAGNETIC PARTICLE IMAGING AND MAGNETIC PARTICLE IMAGING DEVICE

CROSS-REFERENCE TO RELATED APPLICATIONS

The present application is based on PCT filing PCT/JP2019/008489, filed Mar. 5, 2019, which claims priority to JP 2018-097384, filed May 21, 2018, the entire contents of each are incorporated herein by reference.

TECHNICAL FIELD

The present invention relates to an electromagnetic device for use in magnetic particle imaging, and to a magnetic particle imaging apparatus.

BACKGROUND ART

As a method of acquiring a tomographic image of a human body, magnetic particle imaging (MPI) is proposed (see Patent Literature 1, for example). In the MPI, it is requested to generate as strong a magnetic field as possible in a space.

In the MPI described in Patent Literature 1, a plurality of pairs of air-core coils are configured to generate magnetic fields to form a linear zero-field region. Further, in this method, the pairs of air-core coils are controlled so that the zero-field region rotates in a θ direction while reciprocating in an r direction in a two-dimensional polar coordinate system. The "zero-field region" as used herein means a region in which the magnetic fields generated by the pairs of air-core coils cancel each other.

In the MPI described in Patent Literature 1, with the above-mentioned configuration, a two-dimensional (2D) tomographic image can be acquired by a principle similar to X-ray computed tomography (CT), that is, by a principle of a back projection method.

CITATION LIST

Patent Literature

[PTL 1] JP 2013-502262 (see, for example, FIG. 4 and FIG. 7)

SUMMARY OF INVENTION

Technical Problem

In the MPI described in Patent Literature 1, as described above, the plurality of air-core coils generate the magnetic fields. However, the magnetic fields generated by the air-core coils are relatively weak, and hence it is difficult to strengthen the magnetic fields to be generated in the space. Further, in this method, as described above, it is required to control the air-core coils so that the zero-field region rotates in the θ direction. Therefore, the coil configuration becomes complicated, and as a result, satisfactory controllability cannot be obtained.

The present invention has been made to solve the above-mentioned problem, and therefore has an object to provide an electromagnetic device for magnetic particle imaging, with which controllability can be increased while an intensity of a magnetic field generated in a space is increased, and a magnetic particle imaging apparatus including the electromagnetic device for magnetic particle imaging.

Solution to Problem

An electromagnetic device for magnetic particle imaging according to the present invention includes: a return yoke having a gap, which extends in a Y direction and forms a magnetic field space, when a width direction of the magnetic field space is defined as an X direction, and a length direction of the magnetic field space is defined as the Y direction; a gradient magnetic field generating unit, which is provided to the return yoke, and which is configured to generate, in the magnetic field space, a gradient magnetic field in the X direction, and to form, in the magnetic field space, a zero-field region extending in the Y direction; an alternating magnetic field generating unit, which is provided to the return yoke, and which is configured to generate an alternating magnetic field in the magnetic field space; and a rotation mechanism configured to rotate, when a direction perpendicular to the X direction and the Y direction is defined as a Z direction, the gradient magnetic field and the alternating magnetic field relative to a subject with the Z direction being a rotation axis.

A magnetic particle imaging apparatus according to the present invention includes the above-mentioned electromagnetic device for magnetic particle imaging.

Advantageous Effects of Invention

According to the present invention, it is possible to obtain the electromagnetic device for magnetic particle imaging, with which the controllability can be increased while the intensity of the magnetic field generated in the space is increased, and the magnetic particle imaging apparatus including the electromagnetic device for magnetic particle imaging.

DESCRIPTION OF EMBODIMENTS

Now, an electromagnetic device for magnetic particle imaging and a magnetic particle imaging apparatus according to exemplary embodiments of the present invention are described with reference to the drawings. In description of the drawings, the same or similar parts are denoted by the same reference symbols, and duplicate description thereof is omitted.

First Embodiment

Figure 1:
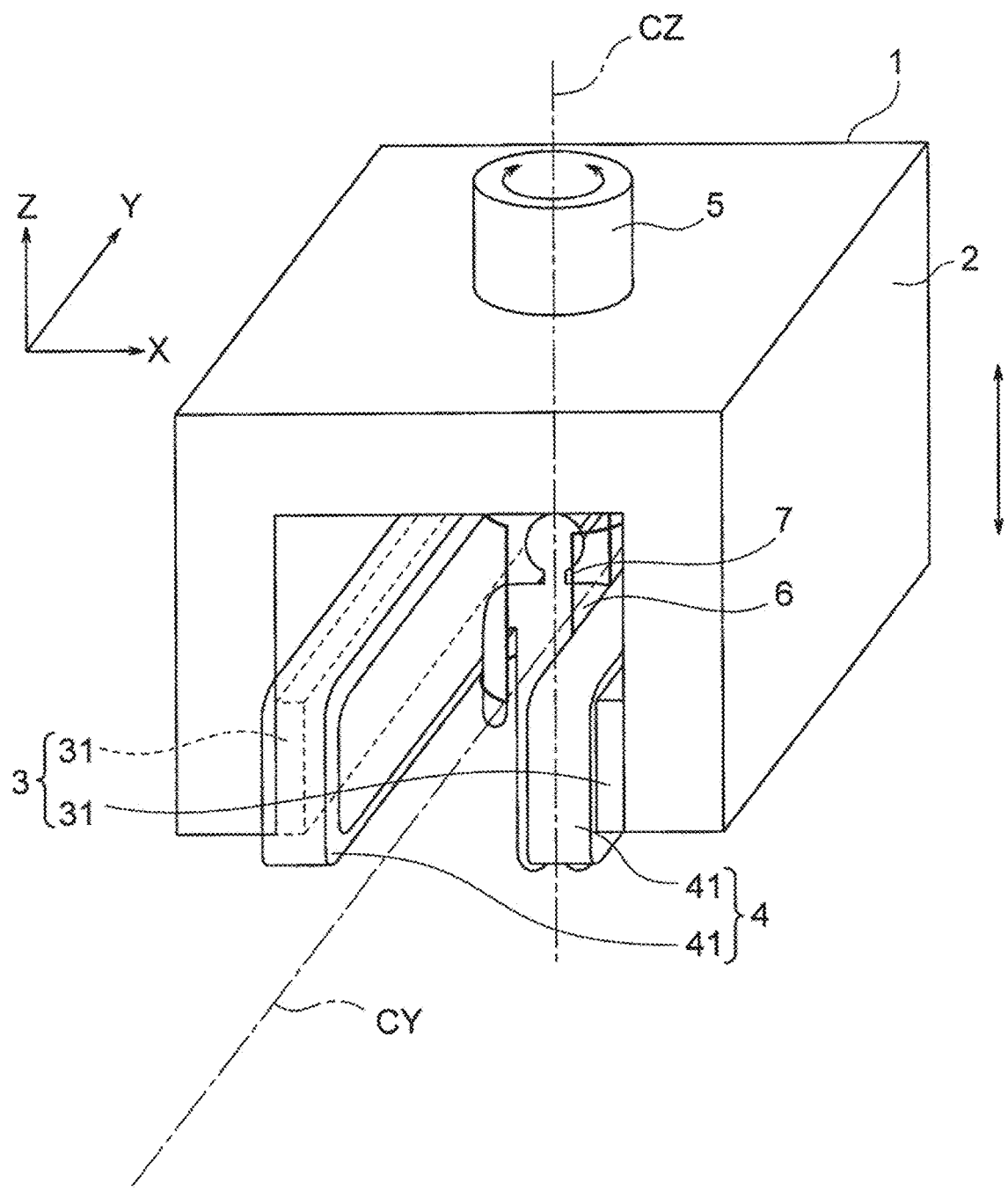
FIG. 1 is a schematic view for illustrating a configuration of an MPI apparatus including an electromagnetic device for MPI according to a first embodiment of the present invention.
Figure 2:
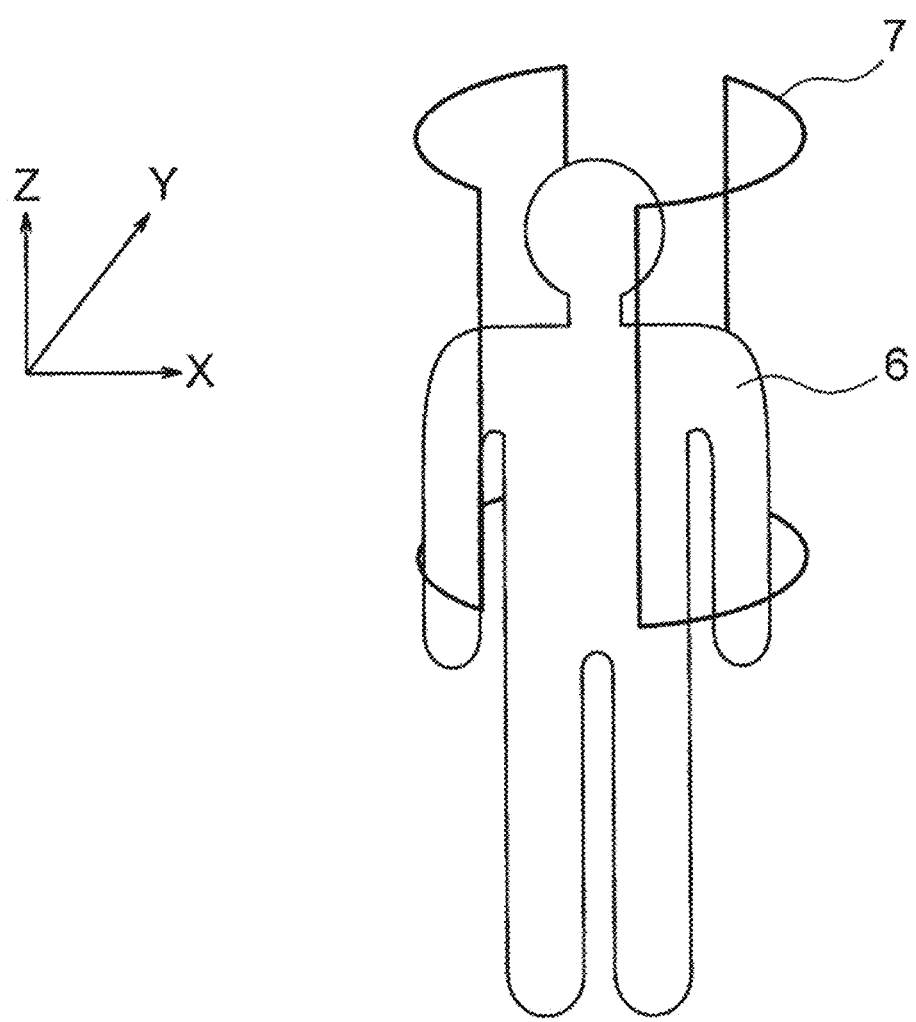
FIG. 2 is a schematic view for illustrating a subject and a receiving coil to be mounted on the subject of FIG. 1.

FIG. 1 is a schematic view for illustrating a configuration of an MPI apparatus including an electromagnetic device 1 for MPI according to a first embodiment for carrying out the present invention. FIG. 2 is a schematic view for illustrating a subject 6 and a receiving coil 7 to be mounted on the subject 6 of FIG. 1.

The MPI apparatus illustrated in FIG. 1 includes the electromagnetic device 1 for MPI (hereinafter abbreviated as "electromagnetic device"), and the receiving coil 7 to be mounted on the subject 6. The electromagnetic device 1 includes a return yoke 2, a gradient magnetic field generating unit 3, an alternating magnetic field generating unit 4, a rotation mechanism, and a movement mechanism.

In the embodiments, a width direction of a magnetic field space is defined as an X direction, a length direction of the magnetic field space is defined as a Y direction, and a direction perpendicular to the X direction and the Y direction is defined as a Z direction. Further, in the embodiments, as a specific example of the subject 6, it is assumed that the subject 6 is a human body.

The return yoke 2 forms a gap, and has the magnetic field space extending in the Y direction. In other words, the return yoke 2 has a gap for forming the magnetic field space extending in the Y direction. The return yoke 2 is formed with the use of a laminated steel plate or other iron plate that is resistant to an eddy current, for example.

The gradient magnetic field generating unit 3 is provided to the return yoke 2. The gradient magnetic field generating unit 3 is configured to generate, in the magnetic field space of the return yoke 2, a gradient magnetic field HX1 in the X direction that changes primarily along the X direction, and to further form, in the magnetic field space, a zero-field region S1 extending in the Y direction.

Specifically, the gradient magnetic field generating unit 3 is configured to generate magnetic fields in a +X direction and a −X direction, to thereby generate the gradient magnetic field HX1. The zero-field region S1 is formed to extend in the Y direction near the center of the magnetic field space when the magnetic fields in the +X direction and the −X direction, which are generated by the gradient magnetic field generating unit 3, cancel each other near the center of the magnetic field space. FIG. 1 shows a zero-field line CY passing through the center of the zero-field region S1 and extending in the Y direction.

As a specific configuration of the gradient magnetic field generating unit 3, the gradient magnetic field generating unit 3 is formed of, for example, as illustrated in FIG. 1, a pair of rectangular permanent magnets 31, which are arranged on the inside, that is, the gap side of the return yoke 2, and which extend in the Y direction to be opposed to each other.

The alternating magnetic field generating unit 4 is provided to the return yoke 2. The alternating magnetic field generating unit 4 is configured to generate, in the magnetic field space of the return yoke 2, an alternating magnetic field HX2 in the X direction that is spatially uniform and changes with time.

As a specific configuration of the alternating magnetic field generating unit 4, the alternating magnetic field generating unit 4 is formed of, for example, as illustrated in FIG. 1, at least one pair of annular alternating magnetic field generating coils 41, which are arranged on the inside of the return yoke 2, and which extend in the Y direction to be opposed to each other. To the pair of alternating magnetic field generating coils 41, a power source configured to energize the pair of alternating magnetic field generating coils 41 is connected.

The rotation mechanism is configured to rotate the gradient magnetic field HX1, which is generated by the gradient magnetic field generating unit 3, and the alternating magnetic field HX2, which is generated by the alternating magnetic field generating unit 4, relative to the subject 6 with the Z direction being a rotation axis. When the gradient magnetic field HX1 and the alternating magnetic field HX2 are rotated as described above, the zero-field region S1 is also rotated with the Z direction being a rotation axis.

As a specific configuration of the rotation mechanism, the rotation mechanism is configured, for example, to rotate the return yoke 2 with respect to the subject 6, which is stationary. In other words, the rotation mechanism is configured, as illustrated in FIG. 1, to rotate the return yoke 2 with a center axis of the return yoke 2 in the Z direction being a rotation axis CZ, to thereby rotate the gradient magnetic field HX1 and the alternating magnetic field HX2. The rotation axis CZ is perpendicular to each of the zero-field region S1 and the zero-field line CY, and corresponds to a body axis of the subject 6. When the return yoke 2 is rotated, the gradient magnetic field generating unit 3 and the alternating magnetic field generating unit 4, which are provided to the return yoke 2, are also rotated, and as a result, the gradient magnetic field HX1 and the alternating magnetic field HX2 are rotated. The rotation mechanism is formed, for example, with the use of a motor 5.

The movement mechanism is configured to move the gradient magnetic field HX1, which is generated by the gradient magnetic field generating unit 3, and the alternating magnetic field HX2, which is generated by the alternating magnetic field generating unit 4, in the Z direction relative to the subject 6. When the gradient magnetic field HX1 and the alternating magnetic field HX2 are moved as described above, the zero-field region S1 is also moved in the Z direction.

As a specific configuration of the movement mechanism, the movement mechanism is configured, for example, to move the return yoke 2 with respect to the subject 6, which is stationary. In other words, the movement mechanism is configured, as illustrated in FIG. 1, to move the return yoke 2 in the Z direction, that is, in an up and down direction of the drawing sheet, to thereby move the gradient magnetic field HX1 and the alternating magnetic field HX2 in the Z direction. When the return yoke 2 is moved, the gradient magnetic field generating unit 3 and the alternating magnetic field generating unit 4, which are provided to the return yoke 2, are also moved, and as a result, the gradient magnetic field HX1 and the alternating magnetic field HX2 are moved. As a drive system of the movement mechanism, for example, a rack and pinion system is adopted.

The receiving coil 7 is formed, for example, as illustrated in FIG. 2, of a pair of saddle-shaped coils. The receiving coil 7 is configured to detect magnetization in the X direction of magnetic particles present in the subject 6, which is located in the magnetic field space of the return yoke 2.

Figure 3:
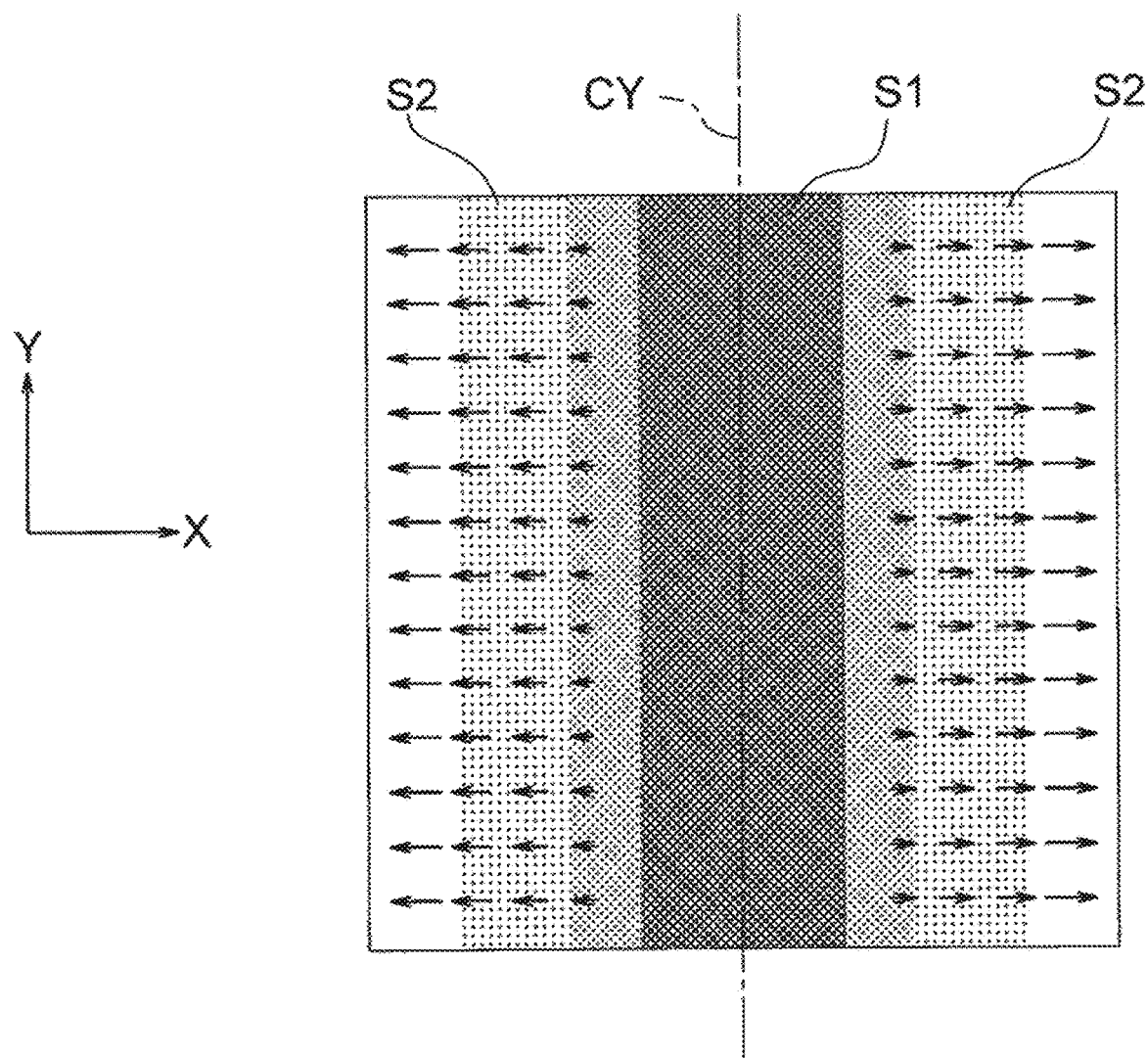
FIG. 3 is a schematic diagram for illustrating how magnetic fields are generated in a +X direction and a −X direction by a gradient magnetic field generating unit of FIG. 1.
Figure 4:
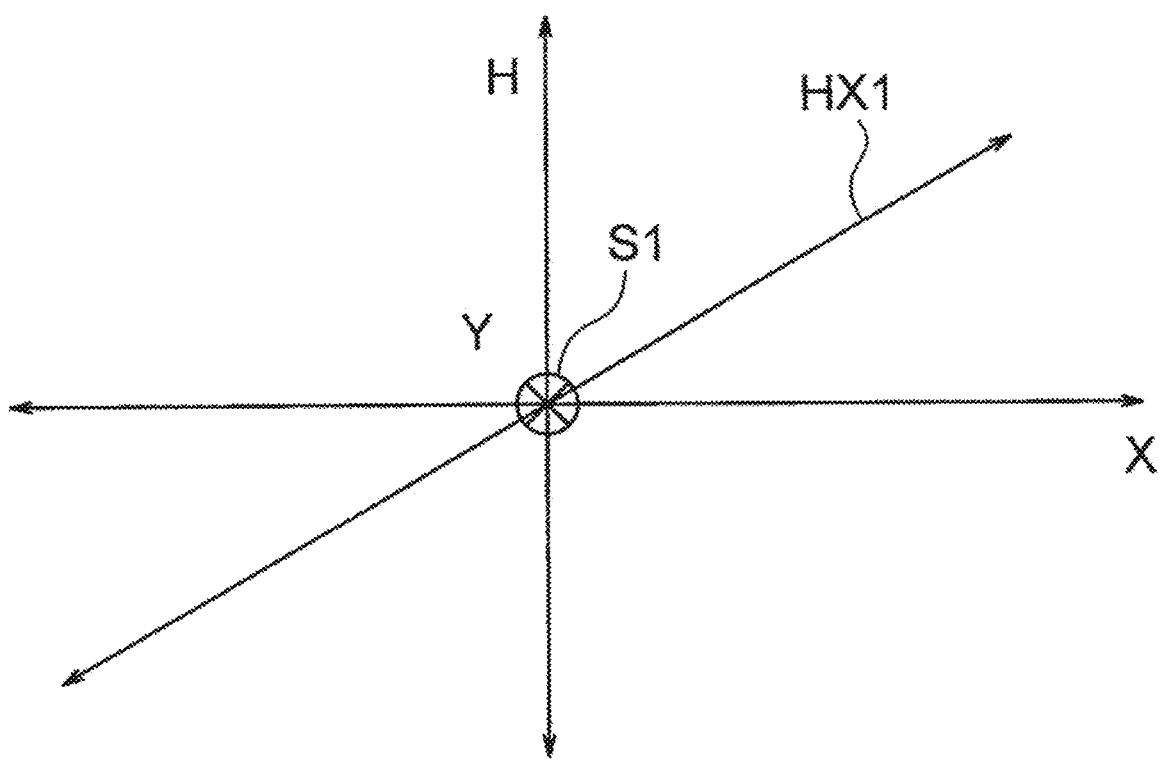
FIG. 4 is a schematic graph for showing a change along an X direction of a gradient magnetic field generated by the gradient magnetic field generating unit of FIG. 1.

Next, an example of the gradient magnetic field HX1 generated by the gradient magnetic field generating unit 3 is described with reference to FIG. 3 and FIG. 4. FIG. 3 is a schematic diagram for illustrating how the magnetic fields are generated in the +X direction and the −X direction by the gradient magnetic field generating unit 3 of FIG. 1. FIG. 4 is a schematic graph for showing a change along the X direction of the gradient magnetic field HX1 generated by the gradient magnetic field generating unit 3 of FIG. 1.

As can be seen from FIG. 3, the zero-field region S1 extending in the Y direction spreads in the X direction around the zero-field line CY. In a region S2 other than the zero-field region S1, an intensity of the magnetic field in the +X direction increases further in the +X direction, and an intensity of the magnetic field in the −X direction increases further in the −X direction. Further, as can be seen from FIG. 4, the gradient magnetic field HX1 changes primarily along the X direction.

In the case where the gradient magnetic field generating unit 3 is formed of the above-mentioned pair of permanent magnets 31, when a length in the Y direction of each permanent magnet 31 is longer than a gap in the X direction of the pair of permanent magnets 31, the gradient magnetic field HX1 that is uniform in the Y direction can be obtained. In this case, the zero-field region S1 also becomes uniform in the Y direction.

Figure 5:
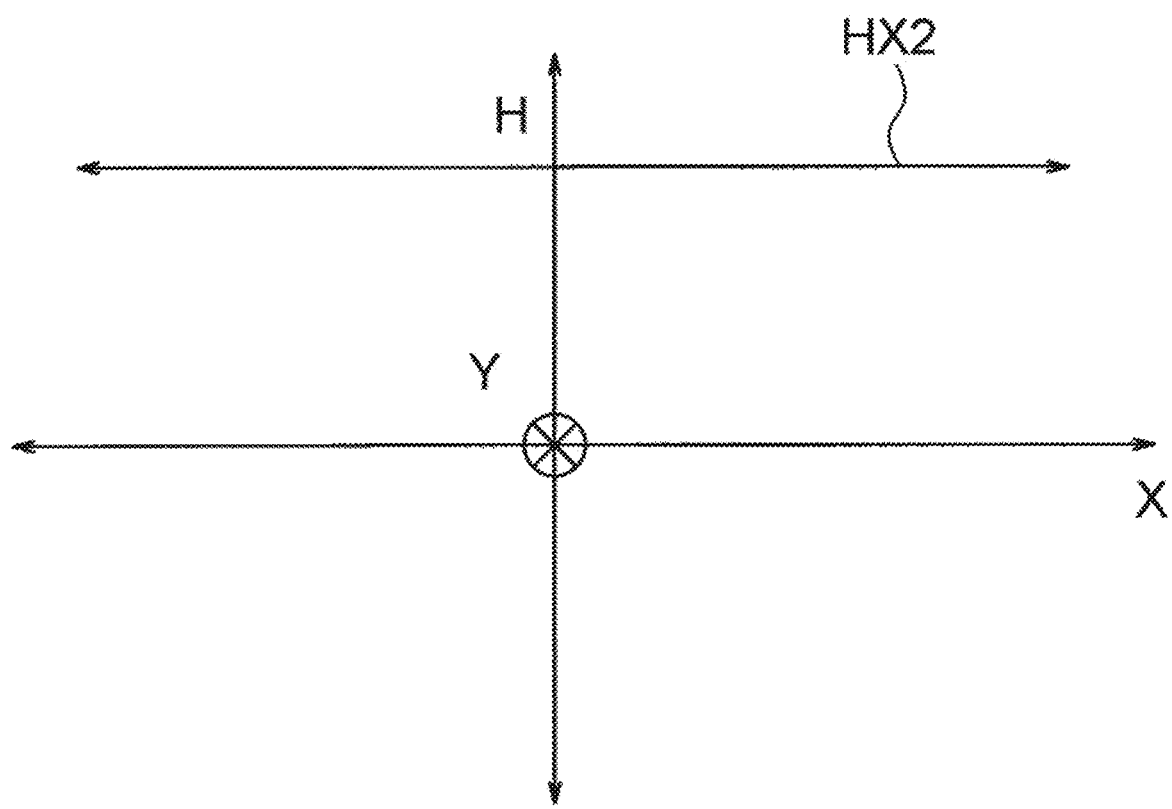
FIG. 5 is a schematic graph for showing a change along the X direction of an alternating magnetic field generated by an alternating magnetic field generating unit of FIG. 1.
Figure 6:
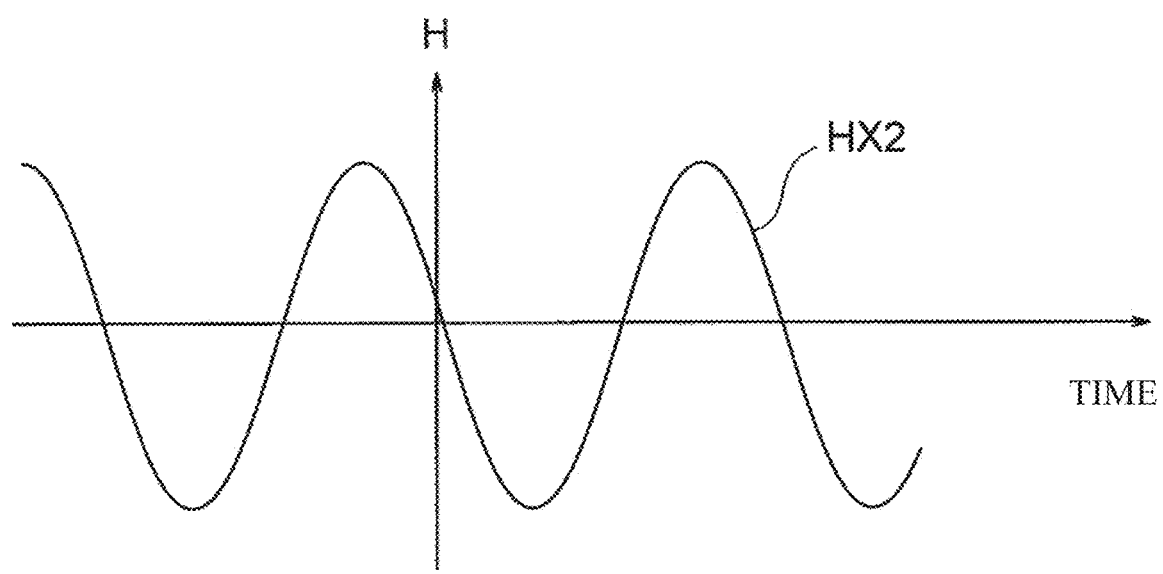
FIG. 6 is a schematic graph for showing a change with time of the alternating magnetic field generated by the alternating magnetic field generating unit of FIG. 1.

Next, an example of the alternating magnetic field HX2 generated by the alternating magnetic field generating unit 4 is described with reference to FIG. 5 and FIG. 6. FIG. 5 is a schematic graph for showing a change along the X direction of the alternating magnetic field HX2 generated by the alternating magnetic field generating unit 4 of FIG. 1. FIG. 6 is a schematic graph for showing a change with time of the alternating magnetic field HX2 generated by the alternating magnetic field generating unit 4 of FIG. 1.

As can be seen from FIG. 5 and FIG. 6, the alternating magnetic field HX2 is uniform along the X direction, and changes with time in a sine wave or a cosine wave.

When the receiving coil 7 is used in the MPI apparatus, it is preferred that a frequency of the alternating magnetic field HX2 be from about 1 kHz to about 20 kHz in terms of receiving sensitivity of the receiving coil 7.

In the first embodiment, the case in which the alternating magnetic field generating unit 4 is configured to generate an alternating magnetic field in the X direction, that is, the alternating magnetic field HX2, is exemplified, but the present invention is not limited thereto. Specifically, the alternating magnetic field generating unit 4 may be configured to generate, instead of the alternating magnetic field HX2, an alternating magnetic field that is perpendicular to the gradient magnetic field HX1, that is, an alternating magnetic field in the Y direction or the Z direction.

Next, the principle of MPI is described. Here, (1) a signal of the magnetic particles that can be obtained along the zero-field region S1 is described first, and (2) a method of acquiring a 2D tomographic image is then described.

Figure 7:
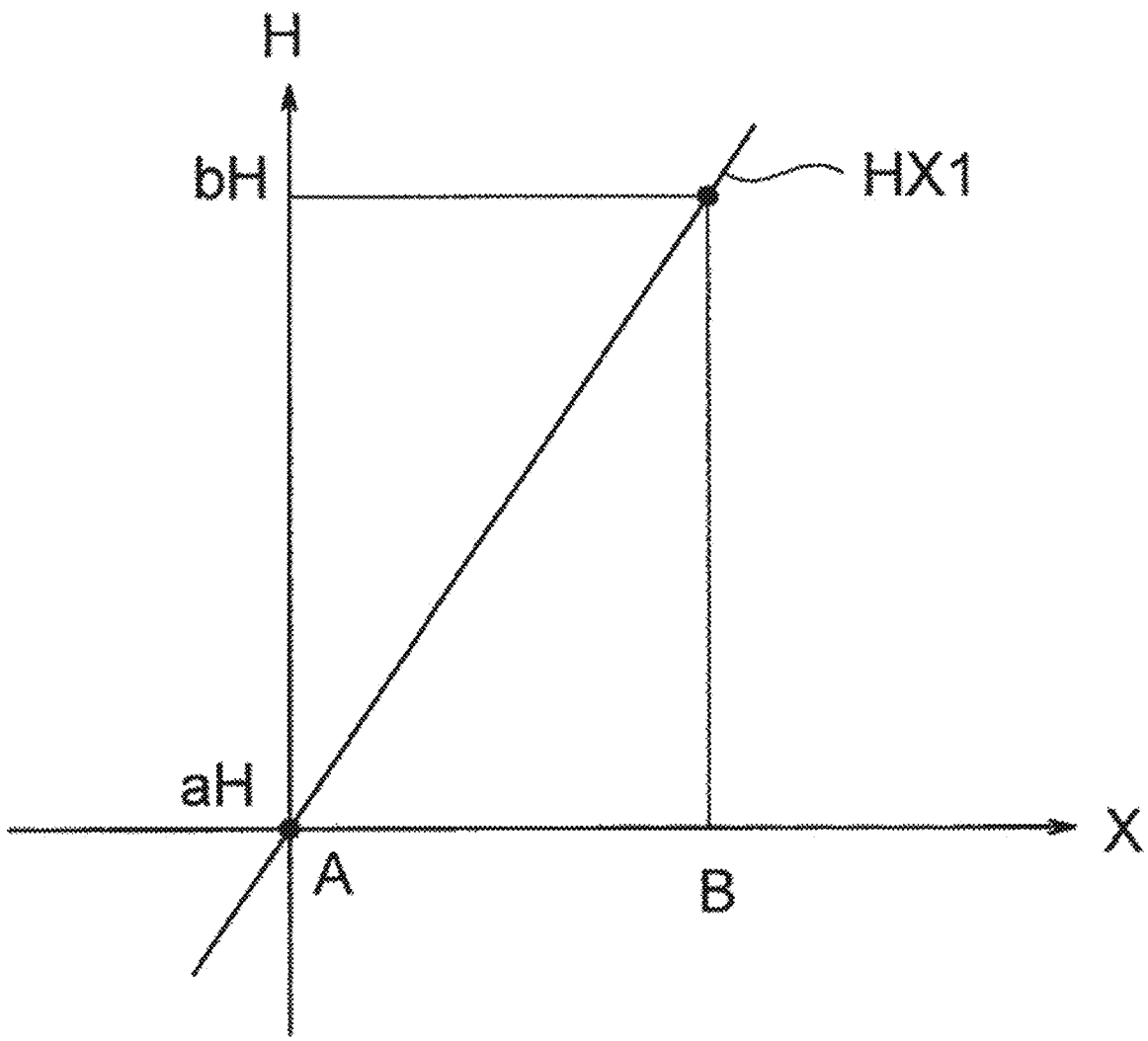
FIG. 7 is a schematic graph for showing magnetic fields received by magnetic particles present in the gradient magnetic field of FIG. 4.
Figure 8:
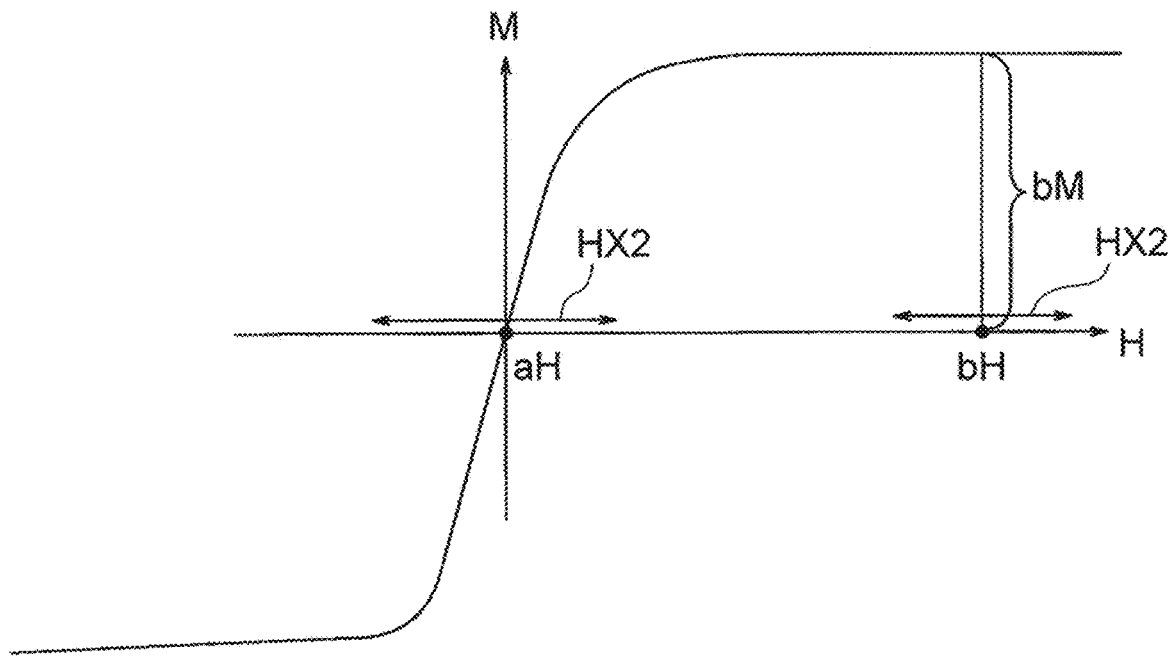
FIG. 8 is a schematic graph for showing an MH curve indicating a relationship between the magnetic fields received by the magnetic particles of FIG. 7 and magnetization of the magnetic particles.

The above-mentioned item (1) is described with reference to FIG. 7 and FIG. 8. FIG. 7 is a schematic graph for showing the magnetic fields received by the magnetic particles present in the gradient magnetic field HX1 of FIG. 4. FIG. 8 is a schematic graph for showing an MH curve indicating a relationship between the magnetic fields received by the magnetic particles of FIG. 7 and the magnetization of the magnetic particles.

There is assumed a case in which the magnetic particles present in the subject 6 are present along the zero-field region S1 extending in the Y direction exemplified in FIG. 3 and FIG. 4. In this case, in the zero-field region S1, the magnetic field is zero, and hence the magnetic particles can move freely. When the alternating magnetic field HX2 is applied to the subject 6 under this state, a magnetic moment of the magnetic particles oscillates in the direction of the alternating magnetic field HX2. When the receiving coil 7 is arranged near the magnetic particles, the receiving coil 7 receives a magnetic flux variation accompanying the oscillation of the magnetic moment, and a voltage is generated in the receiving coil 7 as a result.

Here, as shown in FIG. 7, the gradient magnetic field HX1 increases linearly further in the +X direction. Further, the magnetic field received by magnetic particles present at a position A in the X direction of the zero-field region S1 is a magnetic field aH, and the magnetic field aH is zero. Still further, the magnetic field received by magnetic particles present at a position B in the X direction of the region S2 other than the zero-field region S1 is a magnetic field bH.

When the alternating magnetic field HX2 is not applied to the magnetic particles, as shown in FIG. 8, magnetization of the magnetic particles receiving the magnetic field aH is zero, and magnetization of the magnetic particles receiving the magnetic field bH is magnetization bM.

When the alternating magnetic field HX2 is applied to the magnetic particles, the magnetization of the magnetic particles receiving the magnetic field aH having the alternating magnetic field HX2 superimposed thereon is changed along with a change with time of the alternating magnetic field HX2 in accordance with the MH curve as shown in FIG. 8. Similarly, magnetization of the magnetic particles receiving a magnetic field obtained by the alternating magnetic field HX2 being superimposed on the magnetic field bH is changed along with the change with time of the alternating magnetic field HX2 in accordance with the MH curve.

When the alternating magnetic field HX2 is applied to the magnetic particles as described above, as shown in FIG. 8, magnetization is in an unsaturated state and changes non-linearly for the magnetic particles receiving the magnetic field aH, while magnetization is in a saturated state for the magnetic particles receiving the magnetic field bH irrespective of the alternating magnetic field HX2. The term "saturated state" as used herein means a state in which a magnitude of the magnetization of the magnetic particles does not change, and the term "unsaturated state" means a state in which a magnitude of the magnetization of the magnetic particles changes.

Even when the alternating magnetic field HX2 is applied to the magnetic particles receiving the magnetic field bH, the magnetization of the magnetic particles maintains the saturated state. In this case, a voltage having the same frequency component as that of the alternating magnetic field HX2 is generated in the receiving coil 7. In other words, in this case, a voltage containing only a first-order component is generated in the receiving coil 7.

In contrast, when the alternating magnetic field HX2 is applied to the magnetic particles receiving the magnetic field aH, the magnetization of the magnetic particles transitions from the saturated state to the unsaturated state. Therefore, the magnetization of the magnetic particles changes non-linearly in accordance with the MH curve, and hence a magnetic flux density, that is, a magnetic flux corresponding to the above-mentioned magnetization changes non-linearly out of proportion to the alternating magnetic field HX2. In this case, a voltage having a frequency component obtained by combining the same frequency component as that of the alternating magnetic field HX2 and a third- or higher-order harmonic component is generated in the receiving coil 7.

As described above, when the alternating magnetic field HX2 is applied to the magnetic particles present in the zero-field region S1, the voltage containing the third- or higher-order harmonic component is generated in the receiving coil 7. In contrast, when the alternating magnetic field HX2 is applied to the magnetic particles present in the region S2 other than the zero-field region S1, the voltage containing only the first-order component is generated in the receiving coil 7. Therefore, when the voltage of the third- or higher-order harmonic component generated in the receiving coil 7 is observed, the magnetization of the magnetic particles present in the zero-field region S1 can be detected. In other words, the receiving coil 7 can detect, as accumulated magnetization, the magnetization of the magnetic particles along the zero-field region S1.

The alternating magnetic field HX2 links the receiving coil 7, and hence the voltage of the first-order component caused by the linkage of the alternating magnetic field HX2 is generated in the receiving coil 7. Therefore, the voltage of the first-order component generated in the receiving coil 7 is not observed. The voltage of the third- or higher-order harmonic component generated in the receiving coil 7 is observed with the use of a lockin amplifier, or is observed through Fourier-transforming a voltage signal, for example.

Figure 9:
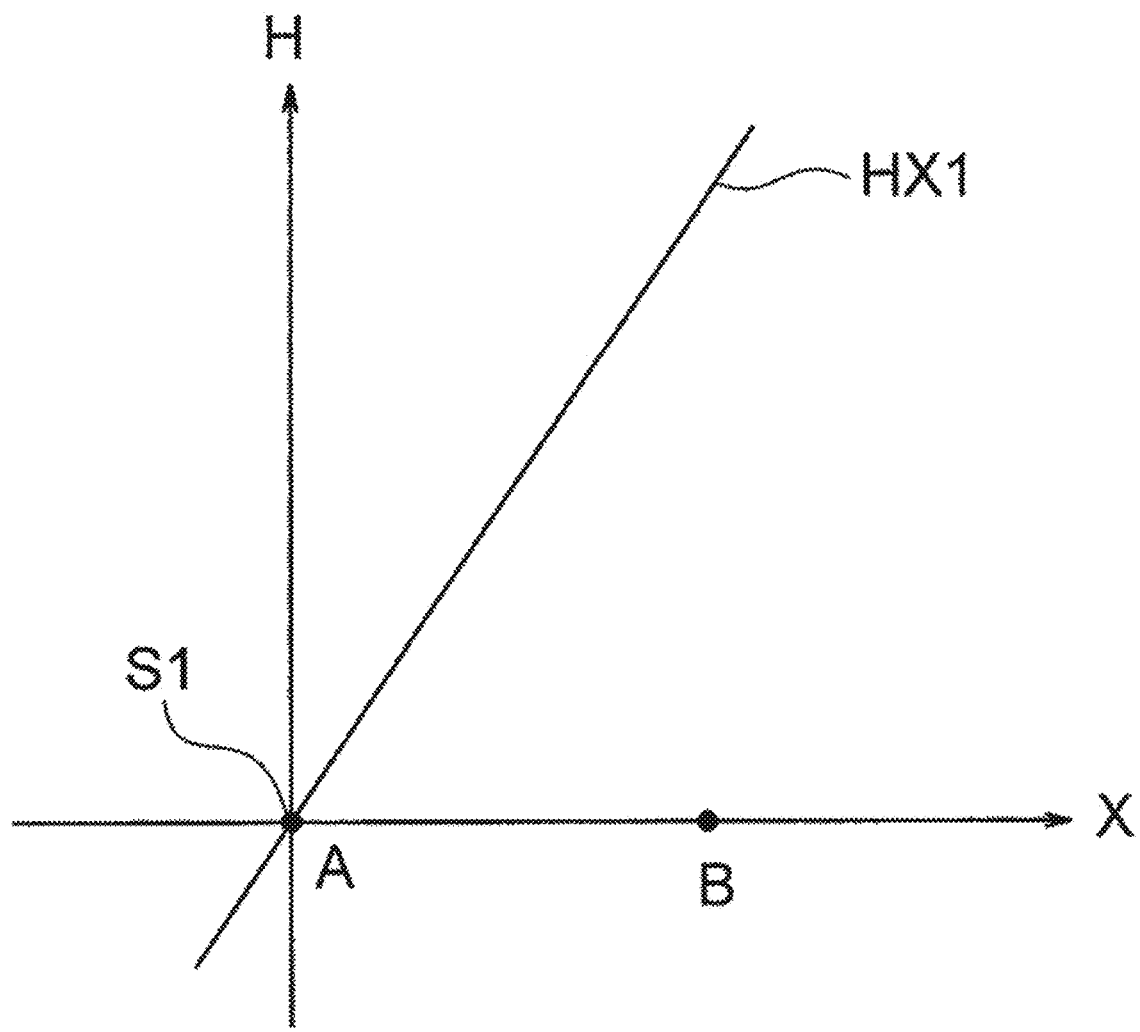
FIG. 9 is a schematic graph for showing the gradient magnetic field of FIG. 7.
Figure 10:
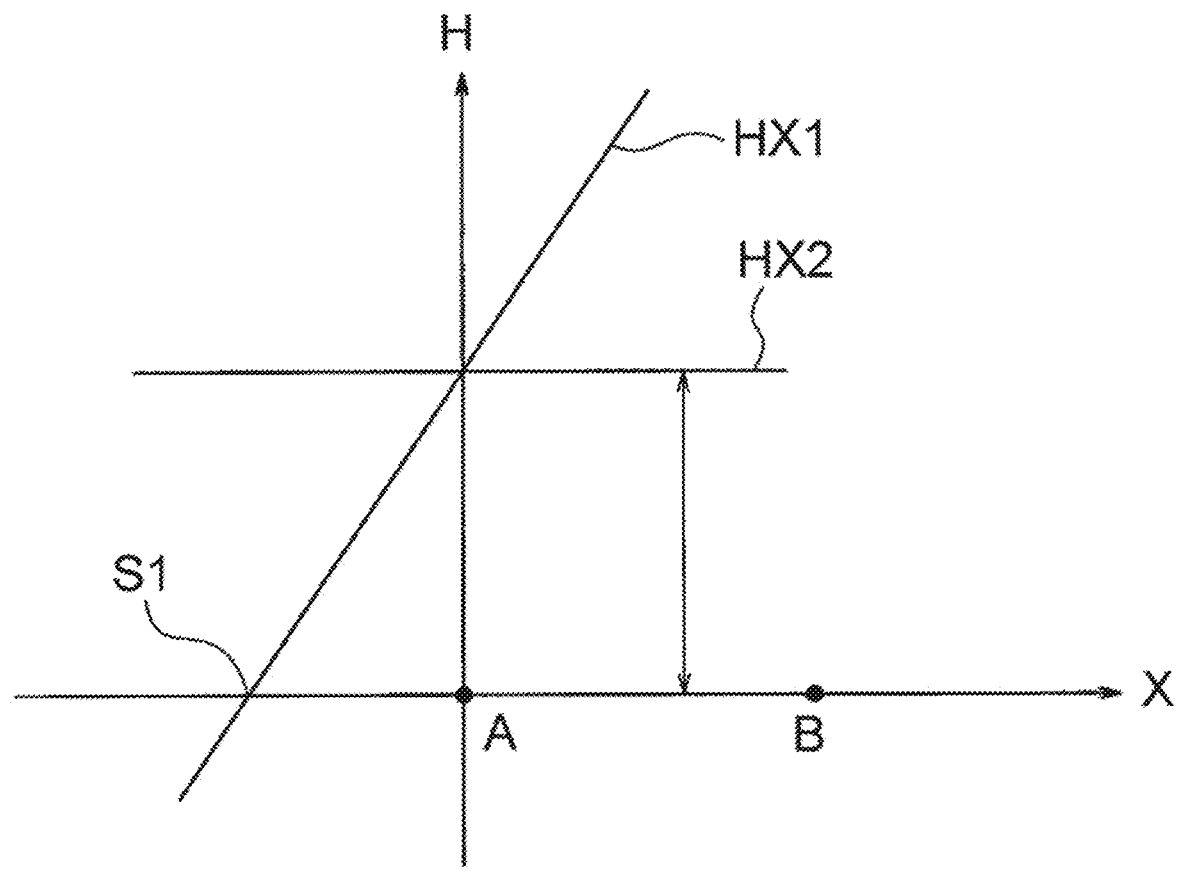
FIG. 10 is a schematic graph for showing a change in gradient magnetic field exhibited when the alternating magnetic field is superimposed on the gradient magnetic field of FIG. 9.

Next, the above-mentioned item (2) is described with reference to FIG. 9 and FIG. 10. FIG. 9 is a schematic graph for showing the gradient magnetic field HX1 of FIG. 7. FIG. 10 is a schematic graph for showing a change in gradient magnetic field HX1 exhibited when the alternating magnetic field HX2 is superimposed on the gradient magnetic field HX1 of FIG. 9.

Here, as described above, in the related art described in Patent Literature 1, in a two-dimensional polar coordinate system, each pair of air-core coils are controlled so that the linear zero-field region rotates in a θ direction while reciprocating in an r direction. As a result, as in X-ray CT, an accumulated magnetization distribution in the R direction and the θ direction is obtained, and a 2D tomographic image is obtained under the principle of a back projection method.

In this embodiment, as can be seen from FIG. 10, with the alternating magnetic field HX2 being superimposed on the gradient magnetic field HX1, the zero-field region S1 moves in the X direction. In other words, when the alternating magnetic field HX2 is not superimposed on the gradient magnetic field HX1 as shown in FIG. 9, the zero-field region S1 is located at the position A.

In contrast, as shown in FIG. 10, when a positive alternating magnetic field HX2 is superimposed on the gradient magnetic field HX1, the zero-field region S1 moves in the −X direction with respect to the position A. When a negative alternating magnetic field HX2 is superimposed on the gradient magnetic field HX1, the zero-field region S1 is moved in the +X direction with respect to the position A.

As described above, with the alternating magnetic field HX2 being superimposed on the gradient magnetic field HX1, the zero-field region S1 is moved in the X direction. Further, with the rotation mechanism, the zero-field region S1 is rotated with the Z direction being the rotation axis. In other words, in the first embodiment, as opposed to the related art described in Patent Literature 1, the linear zero-field region can be rotated while being reciprocated without the use of a plurality of pairs of air-core coils.

In this embodiment, the alternating magnetic field generating unit 4 can be formed of at least one pair of annular coils as described above, and hence controllability is improved with a simple structure as compared to the related art described in Patent Literature 1. Further, with the return yoke 2 being made of iron, a stronger magnetic field can be obtained.

Further, when the linear zero-field region is merely rotated while being reciprocated, only a 2D image can be obtained. In the first embodiment, the zero-field region S1 is moved in the Z direction by the movement mechanism, and hence a 3D image can be obtained.

Next, a configuration of the return yoke 2 in this embodiment is described with reference to FIG. 11 to FIG. 16.

Figure 11:
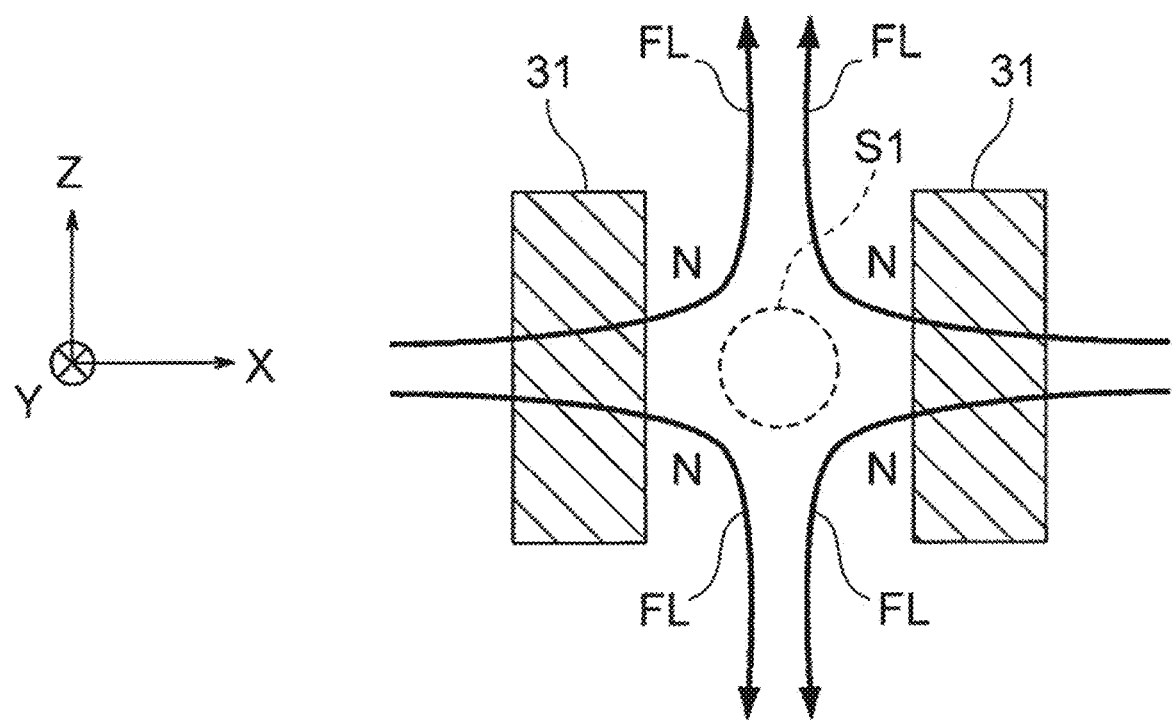
FIG. 11 is a schematic view for schematically illustrating a cross section taken along an XZ plane of a pair of permanent magnets of FIG. 1.

First, the zero-field region S1 formed by the gradient magnetic field generating unit 3 is described with reference to FIG. 11. FIG. 11 is a schematic view for schematically illustrating a cross section taken along an XZ plane of the pair of permanent magnets 31 of FIG. 1. FIG. 11 shows magnetic flux lines FL generated by the permanent magnets 31.

As illustrated in FIG. 11, the pair of permanent magnets 31 are arranged so that N poles are opposed to each other via a gap in the X direction. The magnetic flux lines FL generated by the permanent magnets 31 are originally a large number of lines, but only one line is illustrated representatively in FIG. 11.

In the XZ plane illustrated in FIG. 11, when the center of the gap is X=Z=0, magnetic fields generated from the N poles of the pair of permanent magnets 31 collide and repel each other at the position of X=0, and the zero-field region S1 is formed near the position of X=0 and Z=0. Further, when the pair of permanent magnets 31 are longer in the Y direction than the gap, for example, the zero-field region S1 exists to extend in the Y direction.

Figure 12:
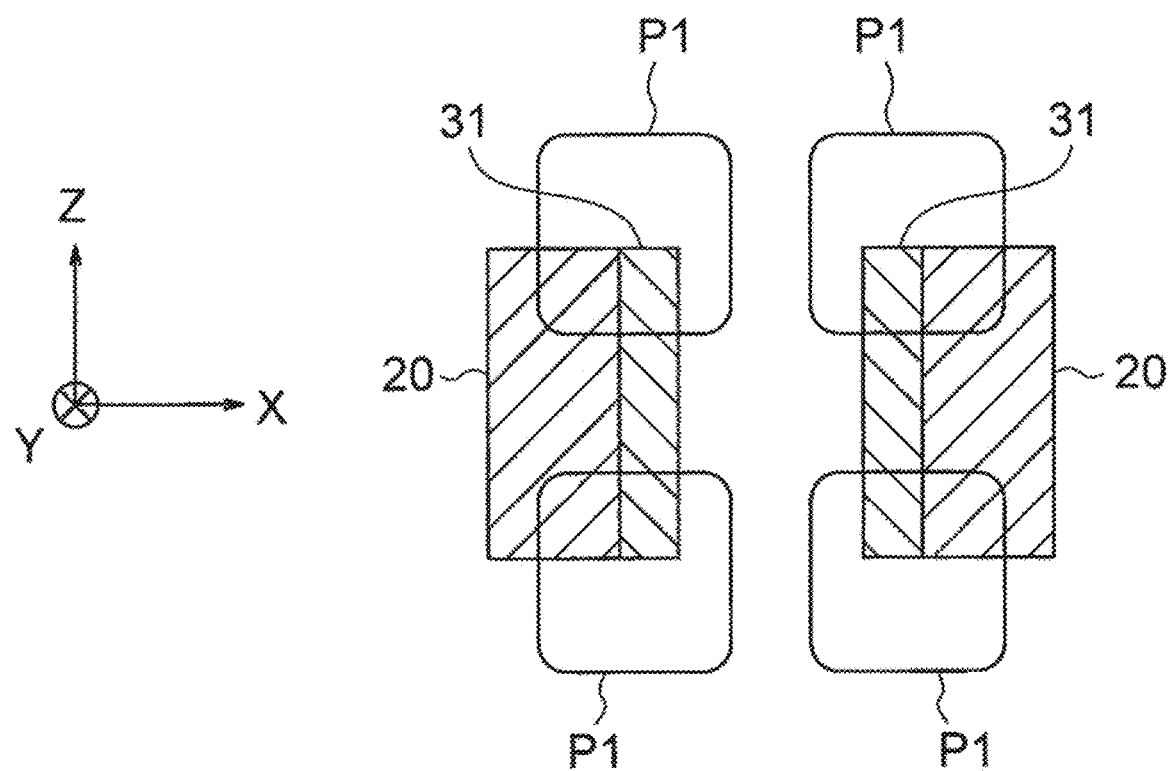
FIG. 12 is a schematic view for illustrating a comparative example for comparison with a return yoke of FIG. 1.
Figure 13:
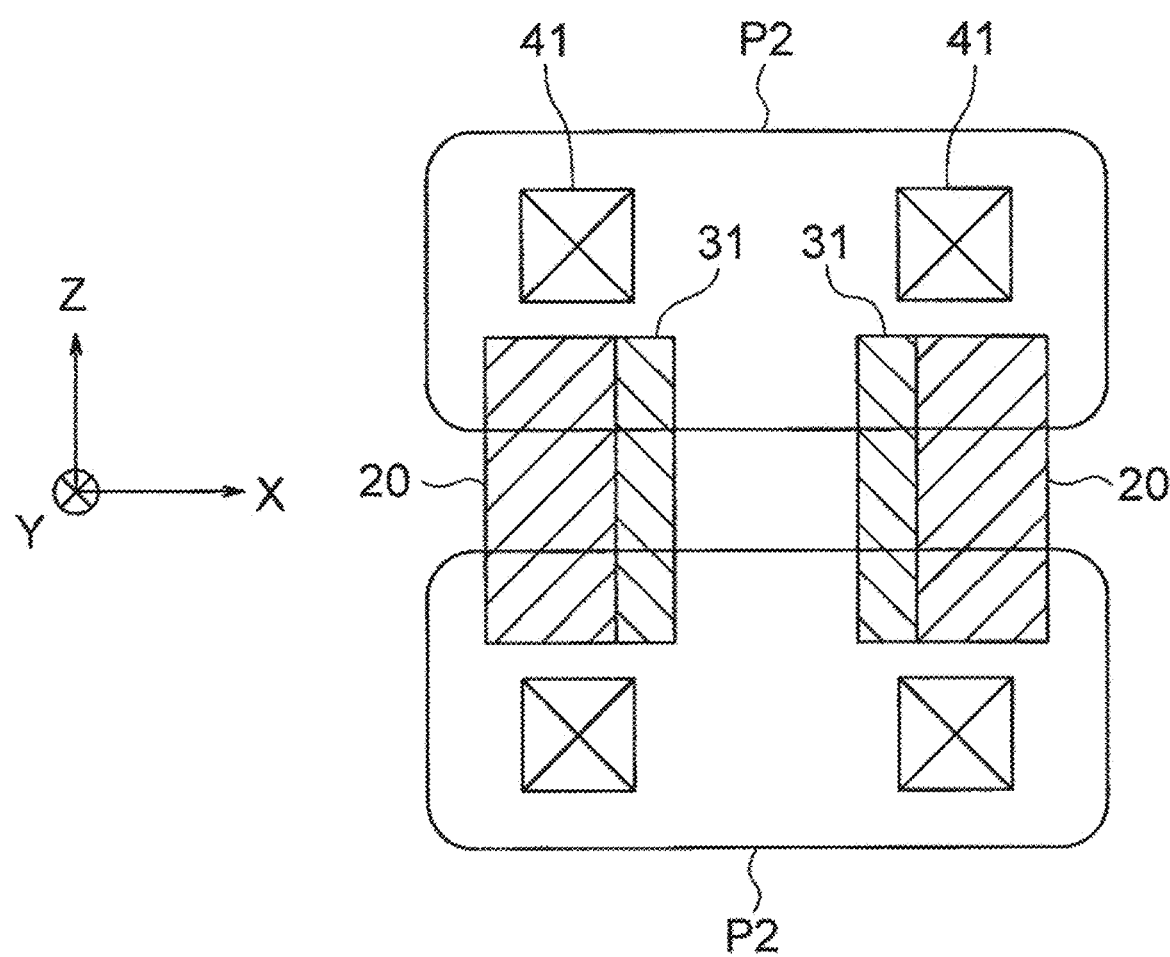
FIG. 13 is a schematic view for illustrating the comparative example for comparison with the return yoke of FIG. 1.

Next, a comparative example for comparison with the return yoke 2 in the first embodiment is described with reference to FIG. 12 and FIG. 13. FIG. 12 and FIG. 13 are schematic views for illustrating the comparative example for comparison with the return yoke 2 of FIG. 1.

FIG. 12 shows magnetic paths P1 generated by the permanent magnets 31, and FIG. 13 shows magnetic paths P2 generated by the alternating magnetic field generating coils 41. Further, as illustrated in FIG. 12 and FIG. 13, as the comparative example, a pair of yokes 20 extending in the Y direction to be opposed to each other are used instead of the return yoke 2.

As illustrated in FIG. 12, the pair of permanent magnets 31 are arranged individually on the pair of yokes 20. In this case, the number of magnetic paths P1 passing through a core with large $\mu$ is large, and as a result, the gradient magnetic field HX1 generated by the permanent magnets 31 is strong.

As illustrated in FIG. 13, the pair of alternating magnetic field generating coils 41 are arranged individually to surround the pair of yokes 20. In this case, most of the magnetic paths P2 exist in an air region having a large magnetic resistance, and as a result, the alternating magnetic field HX2 generated by the alternating magnetic field generating coils 41 is weak.

Therefore, in order to increase the intensities of the gradient magnetic field HX1 and the alternating magnetic field HX2, it is required to contrive the configuration of the return yoke 2 to optimize settings of the magnetic paths P1 and the magnetic paths P2.

Figure 14:
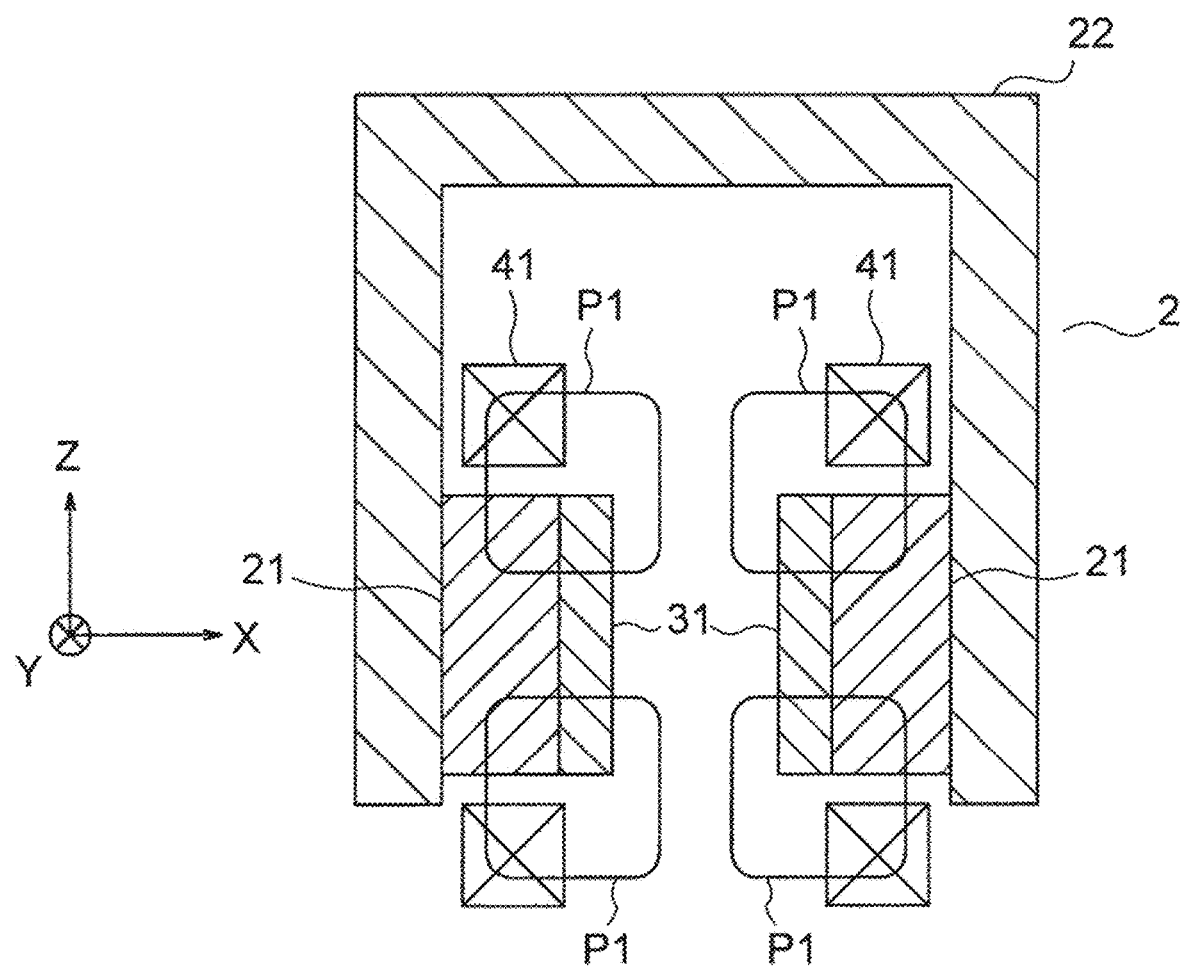
FIG. 14 is a schematic view for schematically illustrating a cross section taken along the XZ plane of the return yoke, the pair of permanent magnets, and a pair of alternating magnetic field generating coils of FIG. 1.
Figure 15:
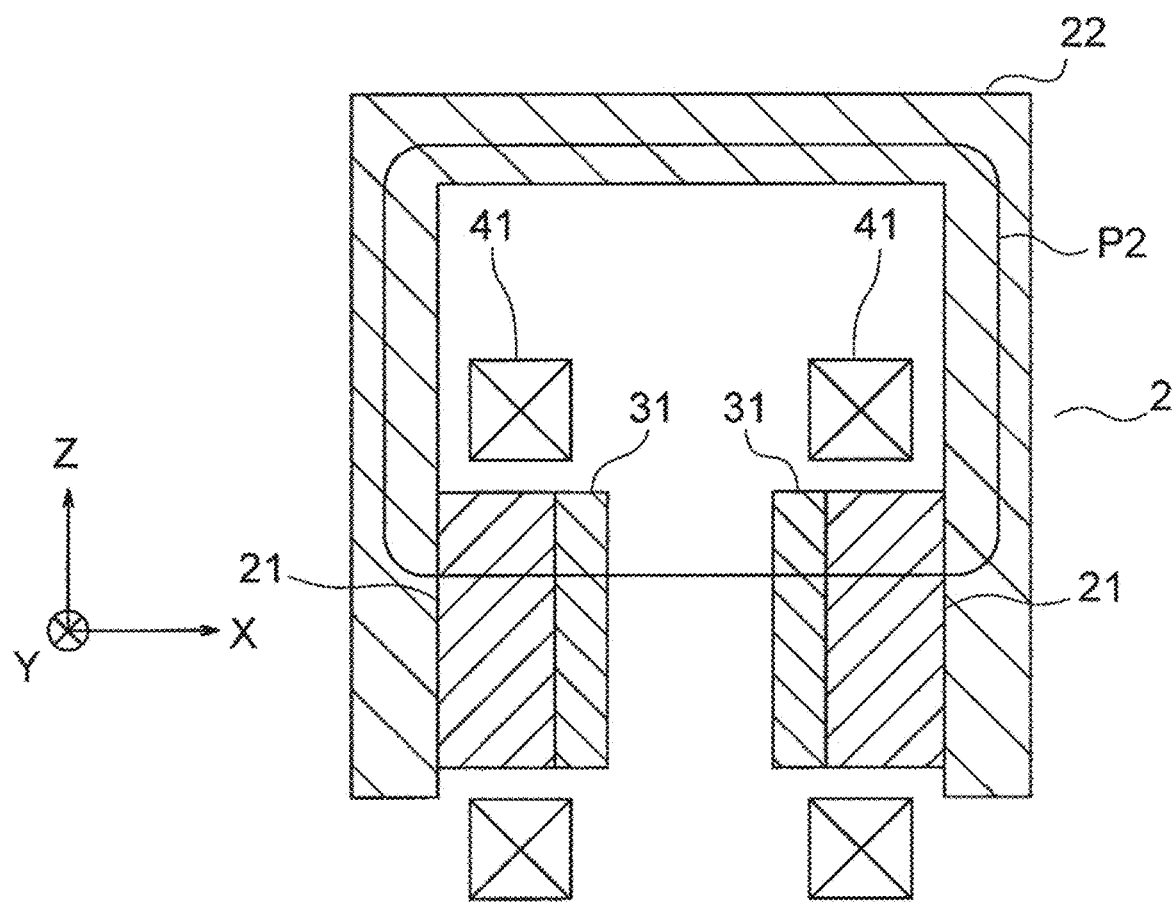
FIG. 15 is a schematic view for schematically illustrating the cross section taken along the XZ plane of the return yoke, the pair of permanent magnets, and the pair of alternating magnetic field generating coils of FIG. 1.

Next, the configuration of the return yoke 2 in this embodiment is described with reference to FIG. 14 and FIG. 15. FIG. 14 and FIG. 15 are schematic views for schematically illustrating a cross section taken along the XZ plane of the return yoke 2, the pair of permanent magnets 31, and the pair of alternating magnetic field generating coils 41 of FIG. 1.

FIG. 14 shows magnetic paths P1 generated by the permanent magnets 31, and FIG. 15 shows magnetic paths P2 generated by the alternating magnetic field generating coils 41.

As illustrated in FIG. 14 and FIG. 15, the return yoke 2 includes an alternating magnetic field yoke 22, which is provided to correspond to the alternating magnetic field HX2, and which extends in the Y direction, and a pair of gradient magnetic field yokes 21, which are provided to correspond to the gradient magnetic field HX1, which are arranged on the inside of the alternating magnetic field yoke 22, and which extend in the Y direction to be opposed to each other. The pair of gradient magnetic field yokes 21 each have a rectangular cross-sectional shape, and the alternating magnetic field yoke 22 has a square-u cross-sectional shape.

The pair of permanent magnets 31 are arranged on the inside of the alternating magnetic field yoke 22, and extend in the Y direction to be opposed to each other. The pair of permanent magnets 31 each have a rectangular cross-sectional shape, and are arranged individually on the pair of gradient magnetic field yokes 21.

The pair of alternating magnetic field generating coils 41 are arranged on the inside of the alternating magnetic field yoke 22, and extend in the Y direction to be opposed to each other. The pair of alternating magnetic field generating coils 41 are arranged individually to surround the pair of gradient magnetic field yokes 21.

As illustrated in FIG. 14, the magnetic paths P1 generated by the permanent magnets 31 pass through the alternating magnetic field generating coils 41 so that energy is minimized because the alternating magnetic field generating coils 41 can be treated as $\mu=1$. Further, as illustrated in FIG. 15, most of the magnetic paths P2 generated by the alternating magnetic field generating coils 41 pass through the alternating magnetic field yoke 22, and hence the alternating magnetic field generating coils 41 can generate a strong magnetic field as compared to the comparative example of FIG. 13.

Figure 16:
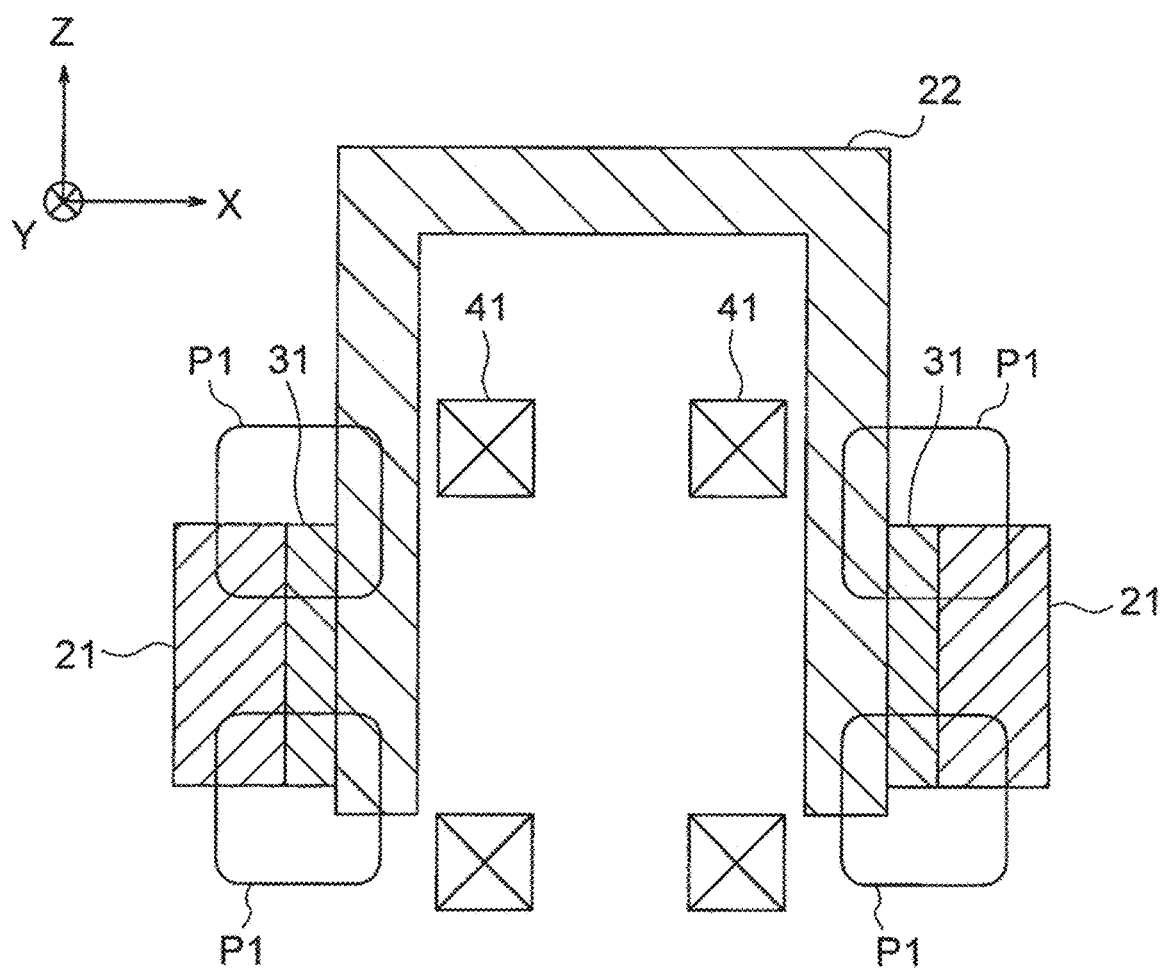
FIG. 16 is a schematic view for illustrating a comparative example of FIG. 14.

Here, as can be seen from a comparative example of FIG. 16, it is important that the gradient magnetic field yokes 21 be arranged on the inside of the alternating magnetic field yoke 22. FIG. 16 is a schematic view for illustrating a comparative example of FIG. 14. FIG. 16 shows magnetic paths P1 generated by the permanent magnets 31.

As illustrated in FIG. 16, when the gradient magnetic field yokes 21 are arranged on the outside of the alternating magnetic field yoke 22, the magnetic paths P1 generated by the permanent magnets 31 pass through the alternating magnetic field yoke 22, and hence the permanent magnets 31 cannot generate the gradient magnetic field HX1.

Therefore, in the first embodiment, as illustrated in FIG. 14, the configuration in which the gradient magnetic field yokes 21 are arranged on the inside of the alternating magnetic field yoke 22 is adopted, and with such a configuration, settings of the magnetic paths P1 and the magnetic paths P2 can be optimized.

As described above, according to the first embodiment, the electromagnetic device for MPI is configured so that, when the width direction of the magnetic field space is defined as the X direction, and the length direction of the magnetic field space is defined as the Y direction, the gradient magnetic field in the X direction is generated in the magnetic field space inside the return yoke to generate, in the magnetic field space, the zero-field region extending in the Y direction, and so that the alternating magnetic field is generated in the magnetic field space. Further, the electromagnetic device for MPI is configured to rotate the gradient magnetic field and the alternating magnetic field relative to the subject with the Z direction being the rotation axis.

As a result, in the electromagnetic device, controllability can be increased while the intensity of the magnetic field generated in the magnetic field space is increased. Further, the electromagnetic device adopts the system in which the return yoke is rotated to rotate the gradient magnetic field and the alternating magnetic field with respect to the subject, which is stationary, so that the coil configuration can be simplified and controllability can be increased. Further, the return yoke is used in the electromagnetic device, and hence a strong magnetic field can be generated in the magnetic field space.

Second Embodiment

In a second embodiment for carrying out the present invention, an electromagnetic device 1 including gradient magnetic field yokes 23 having a different configuration from that of the gradient magnetic field yokes 21 is described as compared to the first embodiment described above. In the second embodiment, description of similarities to the first embodiment described above is omitted, and differences from the first embodiment described above are mainly described.

Figure 17:
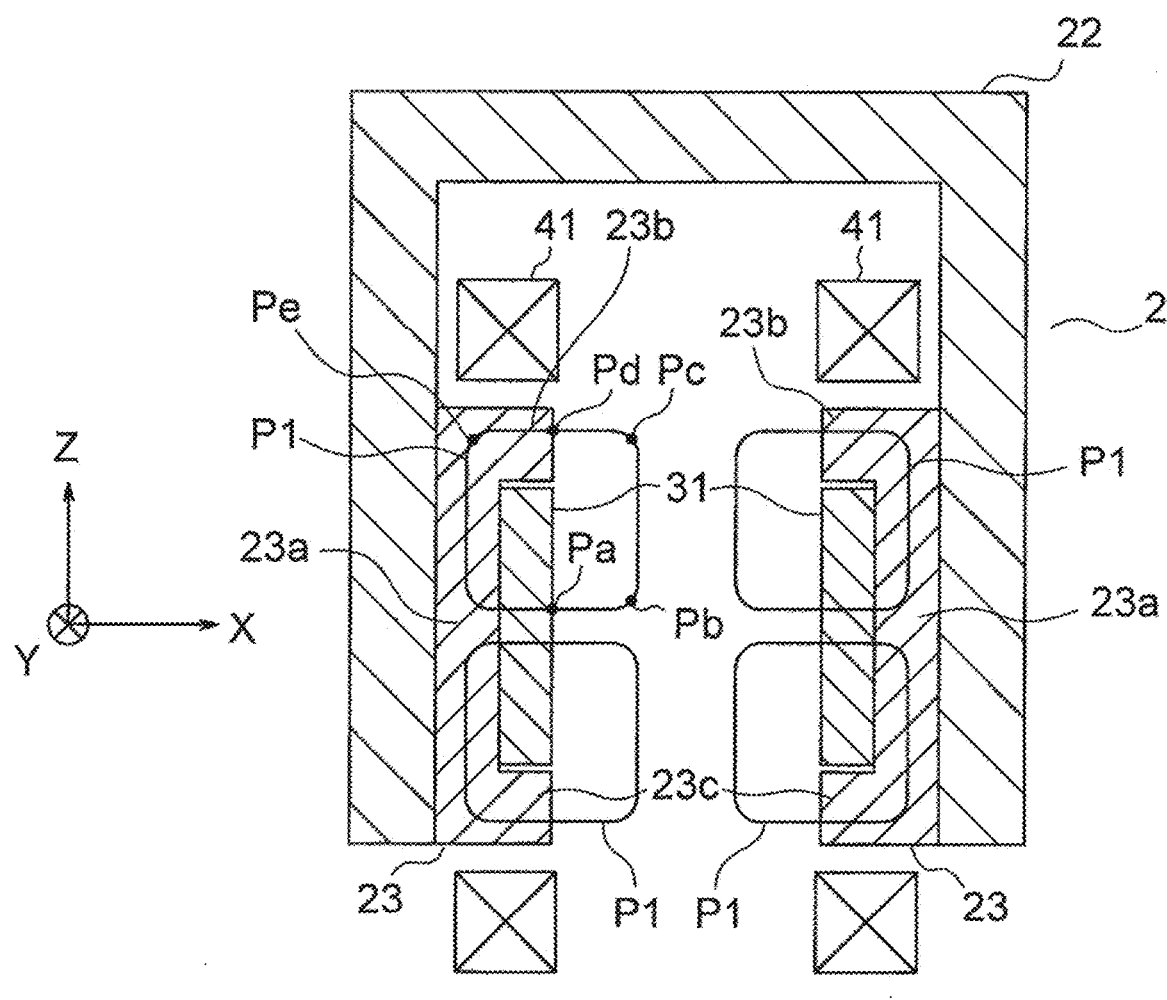
FIG. 17 is a schematic view for schematically illustrating a cross section taken along an XZ plane of a return yoke, a pair of permanent magnets, and a pair of alternating magnetic field generating coils of an electromagnetic device according to a second embodiment of the present invention.
Figure 18:
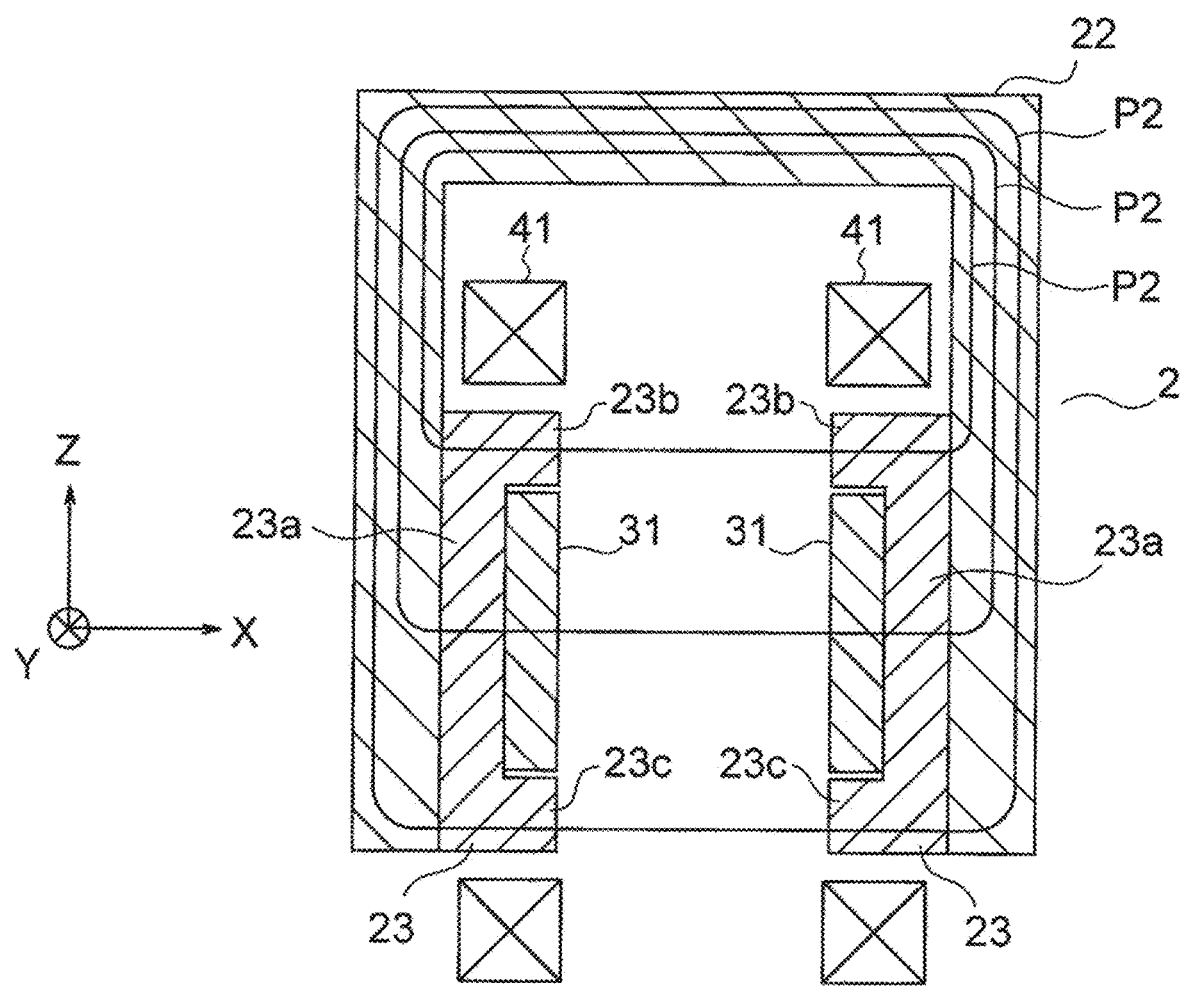
FIG. 18 is a schematic view for schematically illustrating the cross section taken along the XZ plane of the return yoke, the pair of permanent magnets, and the pair of alternating magnetic field generating coils of the electromagnetic device according to the second embodiment.

FIG. 17 and FIG. 18 are schematic views for schematically illustrating a cross section taken along an XZ plane of a return yoke 2, a pair of permanent magnets 31, and a pair of alternating magnetic field generating coils 41 of the electromagnetic device 1 according to the second embodiment.

FIG. 17 shows magnetic paths P1 generated by the permanent magnets 31, and FIG. 18 shows magnetic paths P2 generated by the alternating magnetic field generating coils 41.

As illustrated in FIG. 17 and FIG. 18, a pair of gradient magnetic field yokes 23 extend in the Y direction to be opposed to each other, and each have a square-u cross-sectional shape. Each of the pair of gradient magnetic field yokes 23 has a base portion 23a extending in the Y direction, a first protruding portion 23b protruding in the X direction from one end of the base portion 23a, and a second protruding portion 23c protruding in the X direction from another end of the base portion 23a. The pair of permanent magnets 31 are arranged individually on the base portion 23a of the pair of gradient magnetic field yokes 23.

Here, as opposed to the gradient magnetic field yokes 21 in the first embodiment described above, the first protruding portion 23b and the second protruding portion 23c are formed at both ends of the gradient magnetic field yokes 23.

In this case, the magnetic paths P1 generated by the permanent magnets 31 pass through iron, which has a lower magnetic resistance than that of air, for the first protruding portion 23b and the second protruding portion 23c.

Specifically, as illustrated in FIG. 17, an air region of each magnetic path P1 has the following portions: a magnetic path between Pa and Pb, a magnetic path between Pb and Pc, and a magnetic path between Pc and Pd. In this case, the magnetic path P1 does not pass the air region, which has a high magnetic resistance, for a magnetic path between Pd and Pe as compared to the above-mentioned configuration of FIG. 14. In other words, the magnetic path P1 passes through iron, which has the low magnetic resistance, for the magnetic path between Pd and Pe.

Therefore, the magnetic resistance of the permanent magnets 31 is reduced. As a result, magnetic fluxes corresponding to the magnetic paths P1 become larger, and the gradient magnetic field HX1 becomes stronger. As described above, with the first protruding portion 23b and the second protruding portion 23c, the permanent magnets 31 can generate the stronger gradient magnetic field HX1.

Further, the first protruding portion 23b and the second protruding portion 23c give a good effect on the alternating magnetic field HX2 in addition to the gradient magnetic field HX1. Specifically, as illustrated in FIG. 18, a magnetic path P2 generated by the alternating magnetic field generating coils 41 passes through the first protruding portion 23b, another magnetic path P2 passes through the second protruding portion 23c, and still another magnetic path P2 passes through the base portion 23a.

Figure 19:
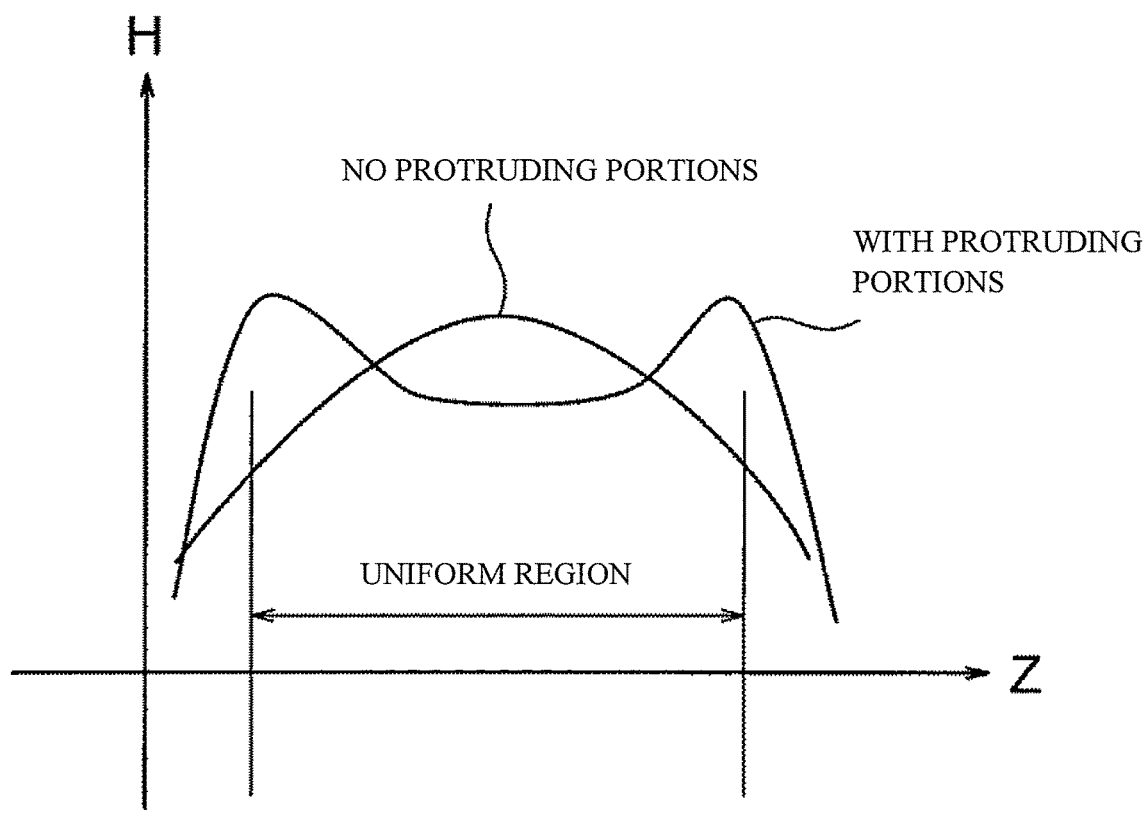
FIG. 19 is a schematic graph for showing a distribution in a Z direction of an alternating magnetic field exhibited in a case where a first protruding portion and a second protruding portion are provided at both ends of each gradient magnetic field yoke of FIG. 18.

Now, distributions of the alternating magnetic field HX2 exhibited in the case where the first protruding portion 23b and the second protruding portion 23c are provided, and in the case where the first protruding portion 23b and the second protruding portion 23c are not provided are described with reference to FIG. 19. FIG. 19 is a schematic graph for showing the distribution in the Z direction of the alternating magnetic field HX2 exhibited in the case where the first protruding portion 23b and the second protruding portion 23c are provided at both ends of each gradient magnetic field yoke 23 of FIG. 18.

FIG. 19 shows, as a comparative example, the distribution in the Z direction of the alternating magnetic field HX2 exhibited in the case where the first protruding portion 23b and the second protruding portion 23c are not provided at both ends of each gradient magnetic field yoke 23 of FIG. 18.

In the case where the first protruding portion 23b and the second protruding portion 23c are not provided, the alternating magnetic field HX2 leaks to the outside from around both end portions in the Z direction of the gradient magnetic field yokes 21 illustrated in FIG. 15 as referenced above. In this case, the distribution in the Z direction of the alternating magnetic field HX2 is a convex distribution as shown in FIG. 19.

In contrast, in the case where the first protruding portion 23b and the second protruding portion 23c are provided, the number of magnetic paths P2 passing through the protruding portions is large as compared to the number of magnetic paths P2 passing through the base portion 23a, and hence a part of the alternating magnetic field HX2 leaking to the outside can be cancelled. In this case, the distribution in the Z direction of the alternating magnetic field HX2 becomes flatter in a uniform region as shown in FIG. 19.

As described above, with the provision of the first protruding portion 23b and the second protruding portion 23c, the uniform alternating magnetic field HX2 can be obtained easily along the Z direction. In particular, through appropriate adjustments of the length in the X direction and the length in the Z direction of each of the first protruding portion 23b and the second protruding portion 23c, a more uniform alternating magnetic field HX2 can be generated.

Figure 20:
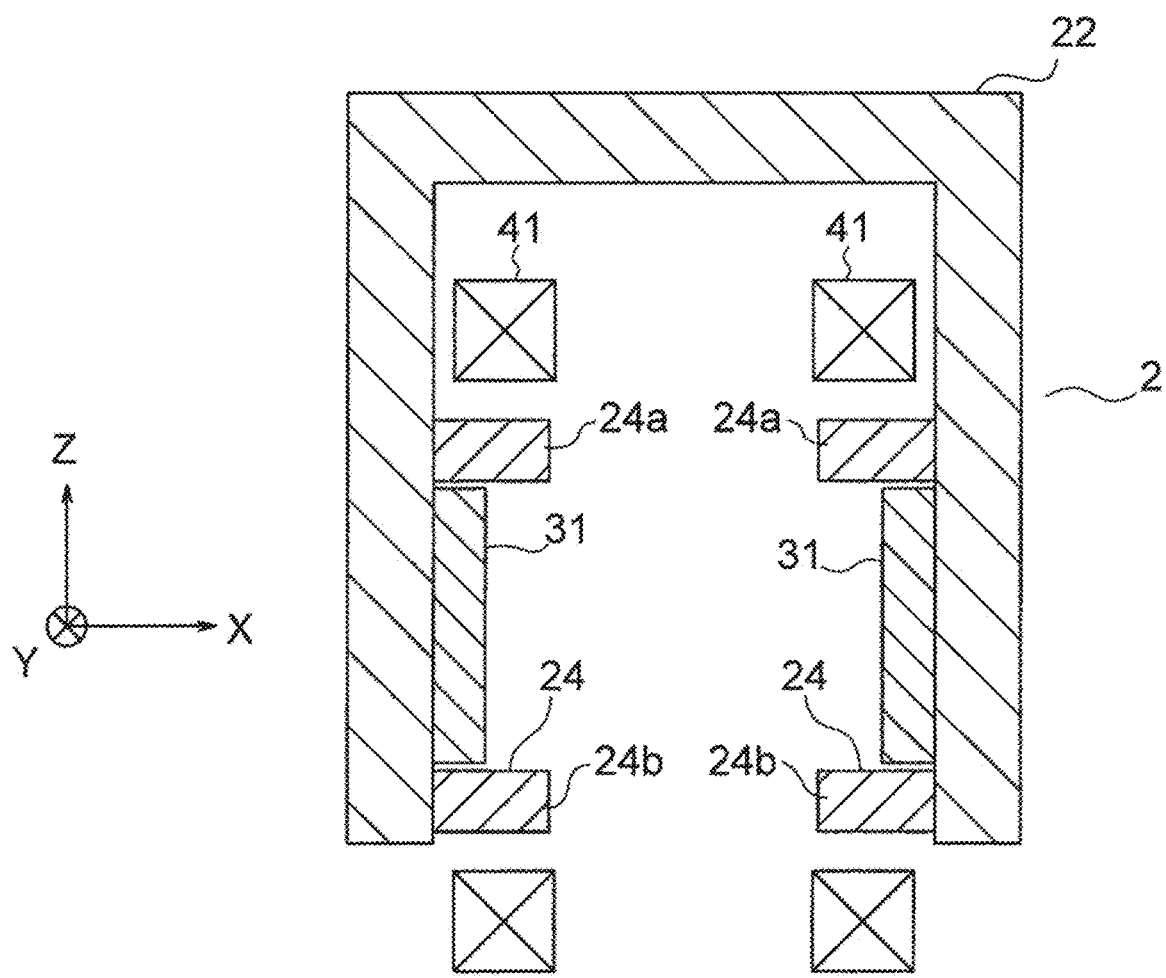
FIG. 20 is a schematic view for illustrating another example of the electromagnetic device according to the second embodiment.

Next, another example of the configuration of the gradient magnetic field yokes 23 in this embodiment is described with reference to FIG. 20. FIG. 20 is a schematic view for illustrating the other example of the electromagnetic device 1 according to the second embodiment. FIG. 20 is a schematic view for showing a cross section taken along an XZ plane of the return yoke 2, the pair of permanent magnets 31, and the pair of alternating magnetic field generating coils 41 in the other example of the electromagnetic device 1.

Here, in the above-mentioned configuration of the gradient magnetic field yokes 23, the first protruding portion 23b and the second protruding portion 23c are provided at both ends of the base portion 23a. In contrast, in a configuration of gradient magnetic field yokes 24 illustrated in FIG. 20, a first protruding portion 24a and a second protruding portion 24b are provided on each inner side surface of the alternating magnetic field yoke 22.

Specifically, as illustrated in FIG. 20, each of a pair of gradient magnetic field yokes 24 has the first protruding portion 24a protruding in the X direction from the inside of the alternating magnetic field yoke 22, and the second protruding portion 24b protruding in the X direction from the inside of the alternating magnetic field yoke 22 to be separated in the Z direction from the first protruding portion 24a.

The pair of permanent magnets 31 are arranged individually on the inner side surfaces of the alternating magnetic field yoke 22, which are opposed to each other, between the first protruding portion 24a and the second protruding portion 24b of each of the pair of gradient magnetic field yokes 24.

As described above, according to this embodiment, in the electromagnetic device for MPI, the shape of each of the pair of gradient magnetic field yokes is contrived as compared to the configuration in the first embodiment described above so that stronger gradient magnetic field and alternating magnetic field can be generated, and the alternating magnetic field having a more uniform distribution in the Z direction can be generated.

Third Embodiment

In a third embodiment for carrying out the present invention, an electromagnetic device 1 different from the first embodiment described above in configuration of the return yoke 2, the gradient magnetic field generating unit 3, and the alternating magnetic field generating unit 4 is described. In the third embodiment, description of similarities to the first and second embodiments described above is omitted, and differences from the first and second embodiments described above are mainly described.

Figure 21:
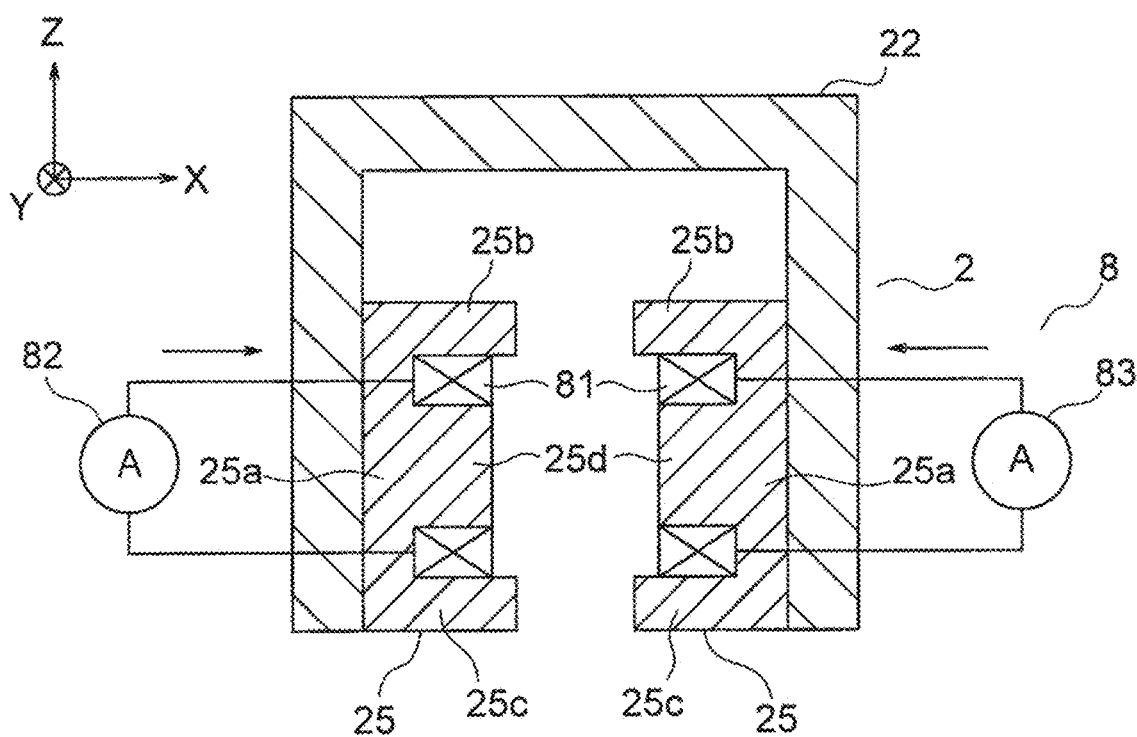
FIG. 21 is a schematic view for schematically illustrating a cross section taken along an XZ plane of a return yoke and a pair of gradient/alternating magnetic field generating coils of an electromagnetic device according to a third embodiment of the present invention.
Figure 22:
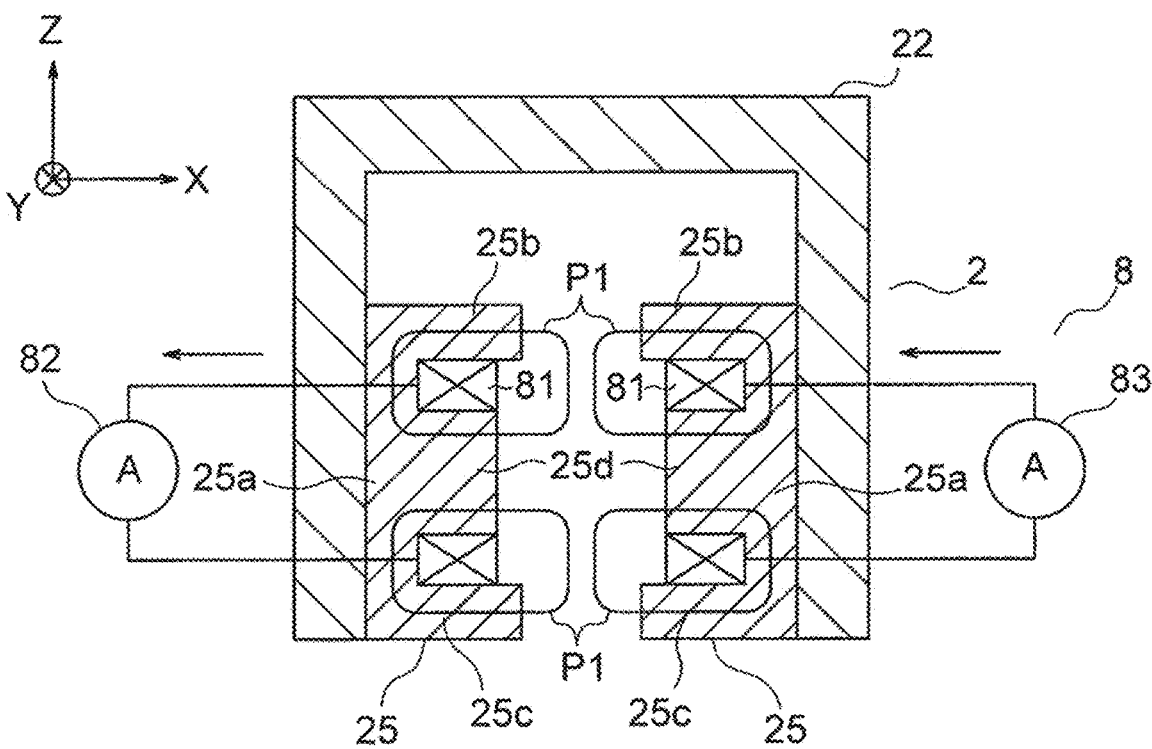
FIG. 22 is a schematic view for schematically illustrating the cross section taken along the XZ plane of the return yoke and the pair of gradient/alternating magnetic field generating coils of the electromagnetic device according to the third embodiment.
Figure 23:
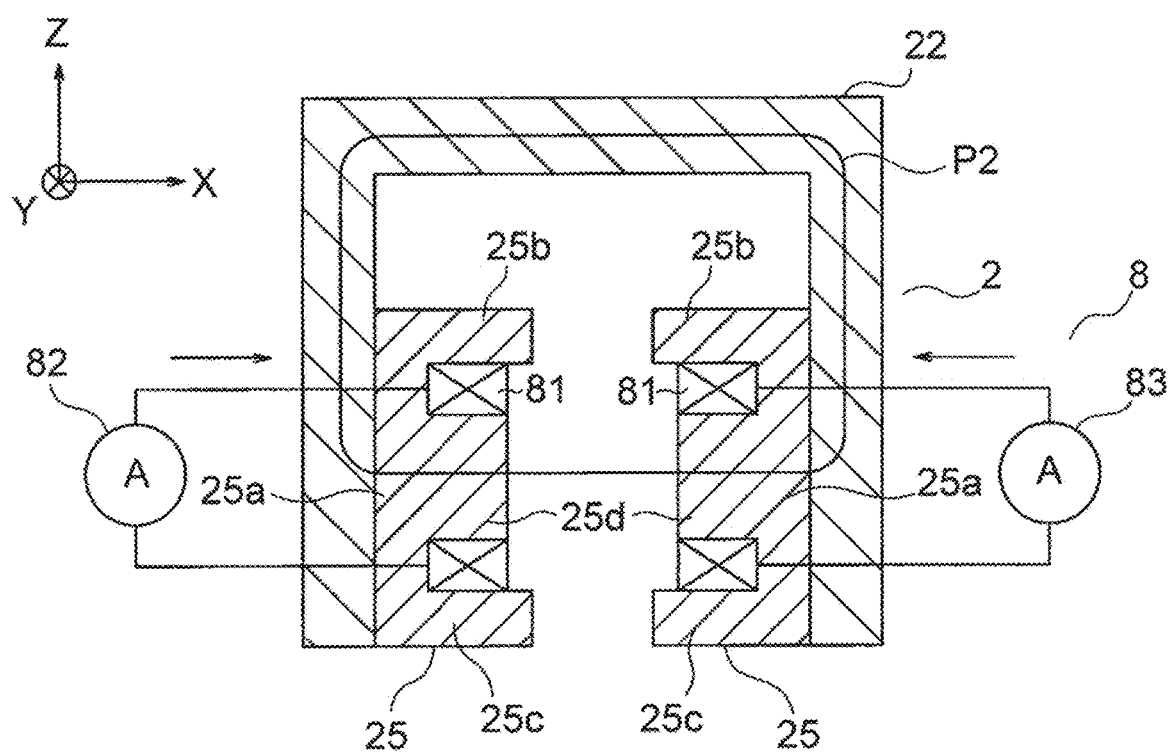
FIG. 23 is a schematic view for schematically illustrating the cross section taken along the XZ plane of the return yoke and the pair of gradient/alternating magnetic field generating coils of the electromagnetic device according to the third embodiment.

FIG. 21 to FIG. 23 are schematic views for schematically illustrating a cross section taken along an XZ plane of a return yoke 2 and a pair of gradient/alternating magnetic field generating coils 81 of the electromagnetic device 1 according to the third embodiment.

FIG. 22 shows magnetic paths P1 generated by the gradient/alternating magnetic field generating coils 81, which is configured to generate a gradient magnetic field and an alternating magnetic field at the same time, and FIG. 23 shows magnetic paths P2 generated by the gradient/alternating magnetic field generating coils 81.

Here, in the first and second embodiments described above, the system in which the gradient magnetic field HX1 is generated by the permanent magnets, and in which the alternating magnetic field HX2 is generated by the coils is adopted. In contrast, in this embodiment, a system in which the gradient magnetic field HX1 and the alternating magnetic field HX2 are generated at the same time by the coils without the use of the permanent magnets is adopted.

As illustrated in FIG. 21 to FIG. 23, the electromagnetic device 1 includes, instead of the gradient magnetic field generating unit 3 and the alternating magnetic field generating unit 4, a gradient/alternating magnetic field generating unit 8 configured to generate the gradient magnetic field HX1 and the alternating magnetic field HX2 in the magnetic field space of the return yoke 2.

The gradient/alternating magnetic field generating unit 8 is formed of the pair of gradient/alternating magnetic field generating coils 81, which are arranged on the inside of the alternating magnetic field yoke 22, and which extend in the Y direction to be opposed to each other.

A pair of gradient magnetic field yokes 25 extend in the Y direction to be opposed to each other, and each have an E cross-sectional shape. Each of the pair of gradient magnetic field yokes 25 has a base portion 25a extending in the Y direction, a first protruding portion 25b protruding in the X direction from one end of the base portion 25a, a second protruding portion 25c protruding in the X direction from another end of the base portion 25a, and a third protruding portion 25d protruding in the X direction from the center of the base portion 25a.

The pair of gradient/alternating magnetic field generating coils 81 are arranged to be inserted individually in the third protruding portions 25d of the pair of gradient magnetic field yokes 25. To the pair of gradient/alternating magnetic field generating coils 81, a pair of power sources 82 and 83 are connected individually. The power source 82 is configured to energize one of the gradient/alternating magnetic field generating coils 81, and the power source 83 is configured to energize another one of the gradient/alternating magnetic field generating coils 81.

It is required that the pair of power sources 82 and 83 pass electric currents I1 in the same direction through the pair of gradient/alternating magnetic field generating coils 81 in order to generate the alternating magnetic field HX2. Further, it is required that the pair of power sources 82 and 83 pass electric currents I2 in opposite directions through the pair of gradient/alternating magnetic field generating coils 81 in order to generate the gradient magnetic field HX1.

Therefore, a total current I caused to flow through the one of the gradient/alternating magnetic field generating coils 81 by the power source 82 and a total current I' caused to flow through the other one of the gradient/alternating magnetic field generating coils 81 by the power source 83 are expressed by the following relational expressions.

$$I=I1+I2$$

$$I'=I1-I2$$

As described above, the electric current I caused to flow through the one of the gradient/alternating magnetic field generating coils 81 by the power source 82 and the electric current I' caused to flow through the other one of the gradient/alternating magnetic field generating coils 81 by the power source 83 are different from each other. As a result, the alternating magnetic field HX2 is generated by current components of the same sign of the electric current I and the electric current I', that is, the electric currents I1, and the gradient magnetic field HX1 is generated by current components of different signs of the electric current I and the electric current I', that is, the electric currents I2.

As illustrated in FIG. 22, the pair of gradient/alternating magnetic field generating coils 81 generate the gradient magnetic field HX1 by the current components of different signs, that is, the electric currents I2, which is accompanied by generation of the magnetic paths P1. In this case, the magnetic paths P1 pass through the gradient magnetic field yokes 25 as in the first and second embodiments described above.

As illustrated in FIG. 23, the pair of gradient/alternating magnetic field generating coils 81 generate the alternating magnetic field HX2 by the current components of the same signs, that is, the electric currents I1, which is accompanied by generation of the magnetic paths P2. In this case, the magnetic paths P2 pass through the alternating magnetic field yokes 22 as in the first and second embodiments described above.

When the yoke is not saturated, the magnetic paths are overlapped with each other. Further, through appropriate adjustments of a length in the X direction and a length in the Z direction of each of the first protruding portion 25b and the second protruding portion 25c, the magnetic field distribution can be manipulated.

Figure 24:
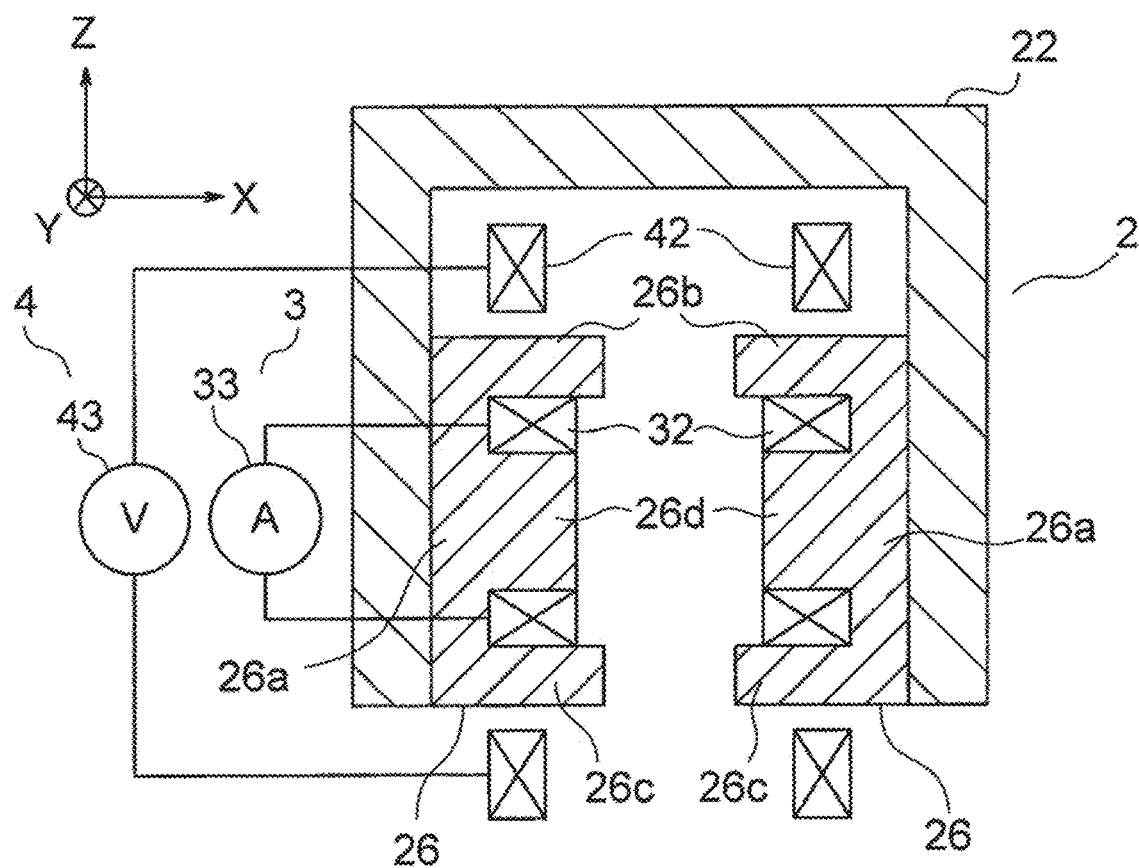
FIG. 24 is a schematic view for illustrating another example of the electromagnetic device according to the third embodiment.

Next, another example of the configuration of the electromagnetic device 1 according to the third embodiment is described with reference to FIG. 24. FIG. 24 is a schematic view for illustrating the other example of the electromagnetic device 1 according to the third embodiment of the present invention. FIG. 24 is a schematic view for illustrating a cross section taken along an XZ plane of the return yoke 2, a pair of gradient magnetic field generating coils 32, and a pair of annular alternating magnetic field generating coils 42 in the other example of the electromagnetic device 1.

As illustrated in FIG. 24, the gradient magnetic field generating unit 3 is formed of the pair of gradient magnetic field generating coils 32, which are arranged on the inside of the alternating magnetic field yoke 22, and which extend in the Y direction to be opposed to each other. The alternating magnetic field generating unit 4 is formed of the pair of annular alternating magnetic field generating coils 42, which are arranged on the inside of the alternating magnetic field yoke 22, and which extend in the Y direction to be opposed to each other.

A pair of gradient magnetic field yokes 26 extend in the Y direction to be opposed to each other, and each have an E cross-sectional shape. Each of the pair of gradient magnetic field yokes 26 has a base portion 26a extending in the Y direction, a first protruding portion 26b protruding in the X direction from one end of the base portion 26a, a second protruding portion 26c protruding in the X direction from another end of the base portion 26a, and a third protruding portion 26d protruding in the X direction from the center of the base portion 26a.

The pair of gradient magnetic field generating coils 32 are arranged to be inserted individually in the third protruding portions 26d of the pair of gradient magnetic field yokes 26. The pair of alternating magnetic field generating coils 42 are arranged individually to surround the pair of gradient magnetic field yokes 26.

The pair of gradient magnetic field generating coils 32 are connected in parallel to each other, and a power source 33, which is a DC power source, is further connected in parallel to the pair of gradient magnetic field generating coils 32. The power source 33 is configured to energize the pair of gradient magnetic field generating coils 32. The pair of gradient magnetic field generating coils 32 are configured to have opposite polarities to each other, and hence can generate the gradient magnetic field HX1 when being energized by the power source 33.

The pair of alternating magnetic field generating coils 42 are connected in parallel to each other, and a power source 43, which is an AC power source, is further connected in parallel to the pair of alternating magnetic field generating coils 42. The pair of alternating magnetic field generating coils 42 are configured so that the electric currents in the same direction flow therethrough, and hence can generate the alternating magnetic field HX2 when being energized by the power source 43.

As described above, according to the third embodiment, even when the gradient magnetic field is generated with the use of the coils instead of the permanent magnets as opposed to the configurations in the first and second embodiments described above, similar effects as those in the first and second embodiments described above can be obtained.

Fourth Embodiment

In a fourth embodiment for carrying out the present invention, an electromagnetic device 1, which adopts a system in which the gradient magnetic field HX1 and the alternating magnetic field HX2 are generated at the same time by coils, and which has a configuration different from that in the third embodiment described above, is described. In the fourth embodiment, description of similarities to the first to third embodiments described above is omitted, and differences from the first to third embodiments described above are mainly described.

Figure 25:
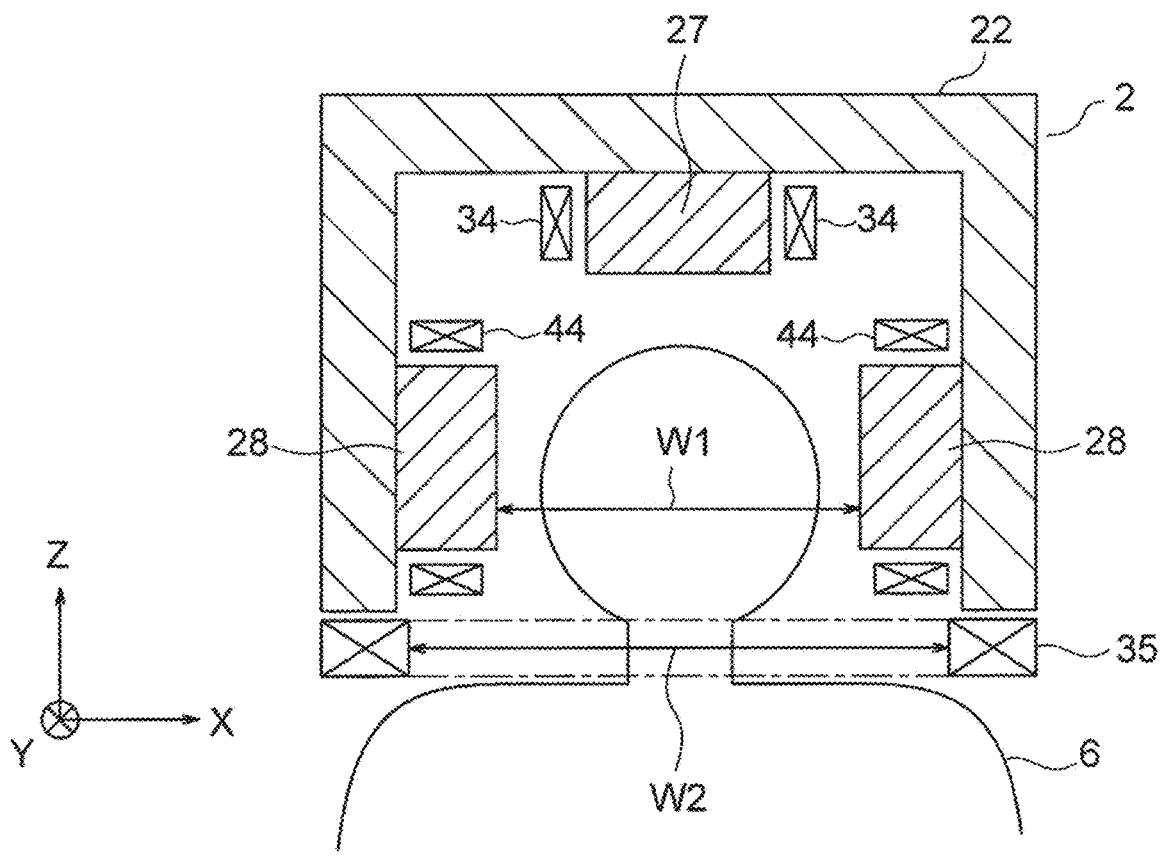
FIG. 25 is a schematic view for schematically illustrating a cross section taken along an XZ plane of a return yoke, an upper gradient magnetic field generating coil, a lower gradient magnetic field generating coil, and a pair of alternating magnetic field generating coils of an electromagnetic device according to a fourth embodiment of the present invention.
Figure 26:
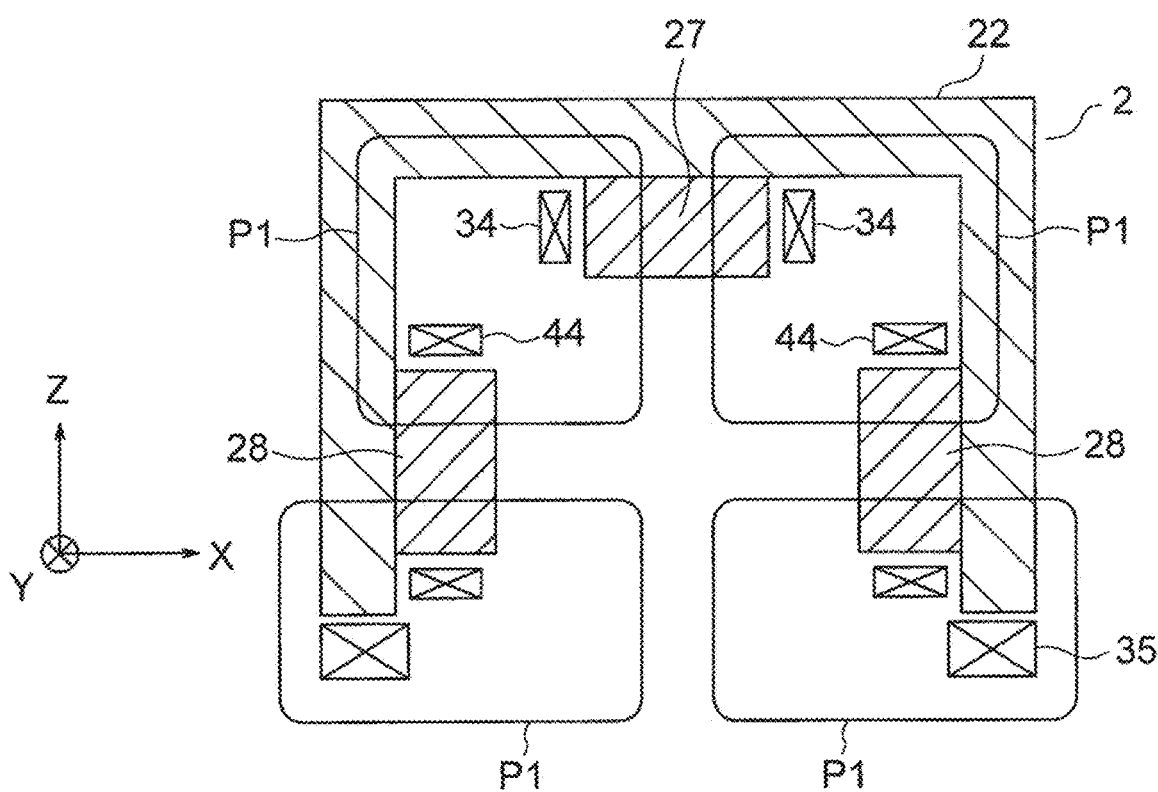
FIG. 26 is a schematic view for schematically illustrating the cross section taken along the XZ plane of the return yoke, the upper gradient magnetic field generating coil, the lower gradient magnetic field generating coil, and the pair of alternating magnetic field generating coils of the electromagnetic device according to the fourth embodiment.
Figure 27:
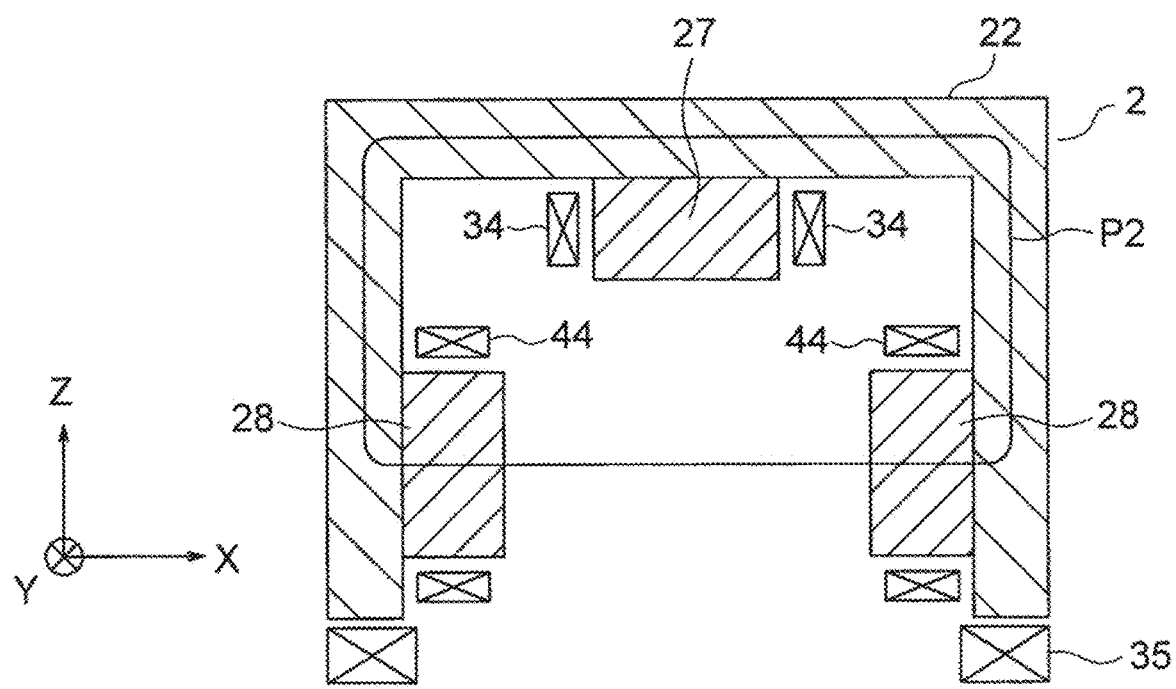
FIG. 27 is a schematic view for schematically illustrating the cross section taken along the XZ plane of the return yoke, the upper gradient magnetic field generating coil, the lower gradient magnetic field generating coil, and the pair of alternating magnetic field generating coils of the electromagnetic device according to the fourth embodiment.

FIG. 25 to FIG. 27 are schematic views for schematically illustrating a cross section taken along an XZ plane of a return yoke 2, an upper gradient magnetic field generating coil 34, a lower gradient magnetic field generating coil 35, and a pair of alternating magnetic field generating coils 44 of the electromagnetic device 1 according to the fourth embodiment.

FIG. 25 shows the subject 6. Further, FIG. 26 shows magnetic paths P1 generated by the upper gradient magnetic field generating coil 34 and the lower gradient magnetic field generating coil 35, and FIG. 27 shows magnetic paths P2 generated by the pair of alternating magnetic field generating coils 44.

As illustrated in FIG. 25 to FIG. 27, the return yoke 2 includes an alternating magnetic field yoke 22 provided to correspond to the alternating magnetic field HX2, and an upper gradient magnetic field yoke 27 and a pair of lower gradient magnetic field yokes 28, which are provided to correspond to the gradient magnetic field HX1. The alternating magnetic field yoke 22 has a square-u cross-sectional shape, the upper gradient magnetic field yoke 27 has a rectangular cross-sectional shape, and the pair of lower gradient magnetic field yokes 28 each have a rectangular cross-sectional shape.

The alternating magnetic field yoke 22 extends in the Y direction. The upper gradient magnetic field yoke 27 is arranged on the inside of the alternating magnetic field yoke 22, and in an upper portion in the Z direction, and extends in the Y direction. The pair of lower gradient magnetic field yokes 28 are arranged on the inside of the alternating magnetic field yoke 22, and in a lower portion in the Z direction, and extend in the Y direction to be opposed to each other. The pair of lower gradient magnetic field yokes 28 are arranged on a lower side of the upper gradient magnetic field yoke 27.

The gradient magnetic field generating unit 3 is formed of an annular upper gradient magnetic field generating coil 34, which is arranged on the inside of the alternating magnetic field yoke 22, and which extends in the Y direction, and an annular lower gradient magnetic field generating coil 35, which is arranged on the outside of the alternating magnetic field yoke 22, and which extends in the Y direction.

The upper gradient magnetic field generating coil 34 is arranged around the upper gradient magnetic field yoke 27. The lower gradient magnetic field generating coil 35 is arranged on a lower side of the upper gradient magnetic field generating coil 34. The upper gradient magnetic field generating coil 34 and the lower gradient magnetic field generating coil 35 are configured so that the electric currents in opposite directions flow therethrough. Therefore, the upper gradient magnetic field generating coil 34 and the lower gradient magnetic field generating coil 35 can generate the gradient magnetic field HX1 when being energized. In the configuration in the fourth embodiment, the upper gradient magnetic field yoke 27 is provided in addition to the configurations in the first to third embodiments described above, and hence a stronger gradient magnetic field HX1 can be generated.

The alternating magnetic field generating unit 4 is formed of the pair of alternating magnetic field generating coils 44, which are arranged on the inside of the alternating magnetic field yoke 22, and which extend in the Y direction to be opposed to each other.

The pair of alternating magnetic field generating coils 44 are arranged individually around the pair of lower gradient magnetic field yokes 28. The pair of alternating magnetic field generating coils 44 are configured so that the electric currents in the same direction flow therethrough. Therefore, the pair of alternating magnetic field generating coils 44 can generate the alternating magnetic field HX2 when being energized.

Here, in a case where the head and other parts of the subject 6 enter the return yoke 2, it is required that a gap width W1 between the pair of lower gradient magnetic field yokes 28 be wide. Further, a human body is generally wider at the shoulders than at the head. Therefore, the electromagnetic device 1 is configured so that the lower gradient magnetic field generating coil 35 is arranged on the outside of the alternating magnetic field yoke 22, and hence an inner width W2 of the lower gradient magnetic field generating coil 35 is wider than the gap width W1 between the pair of lower gradient magnetic field yokes 28. With this configuration, that is, the configuration in which the pair of lower gradient magnetic field yokes 28 and the lower gradient magnetic field generating coil 35 are arranged so that the inner width W2 is wider than the gap width W1, a space in which the shoulders, which are wider than the head, can enter can be secured.

As illustrated in FIG. 26, the upper gradient magnetic field generating coil 34 and the lower gradient magnetic field generating coil 35 generate the gradient magnetic field HX1, which is accompanied by generation of the magnetic paths P1. Further, as illustrated in FIG. 27, the pair of alternating magnetic field generating coils 44 generate the alternating magnetic field HX2, which is accompanied by generation of the magnetic paths P2.

As described above, according to the fourth embodiment, as opposed to the configurations in the first and second embodiments described above, the system in which the gradient magnetic field and the alternating magnetic field are generated at the same time by the coils is adopted, and similar effects to those in the first and second embodiments described above can be obtained even with the configuration different from that of the third embodiment described above.

Fifth Embodiment

In a fifth embodiment for carrying out the present invention, an electromagnetic device 1 different from the first to fourth embodiments described above in configuration of the rotation mechanism and the movement mechanism is described. In the fifth embodiment, description of similarities to the first to fourth embodiments described above is omitted, and differences from the first to fourth embodiments described above are mainly described.

Figure 28:
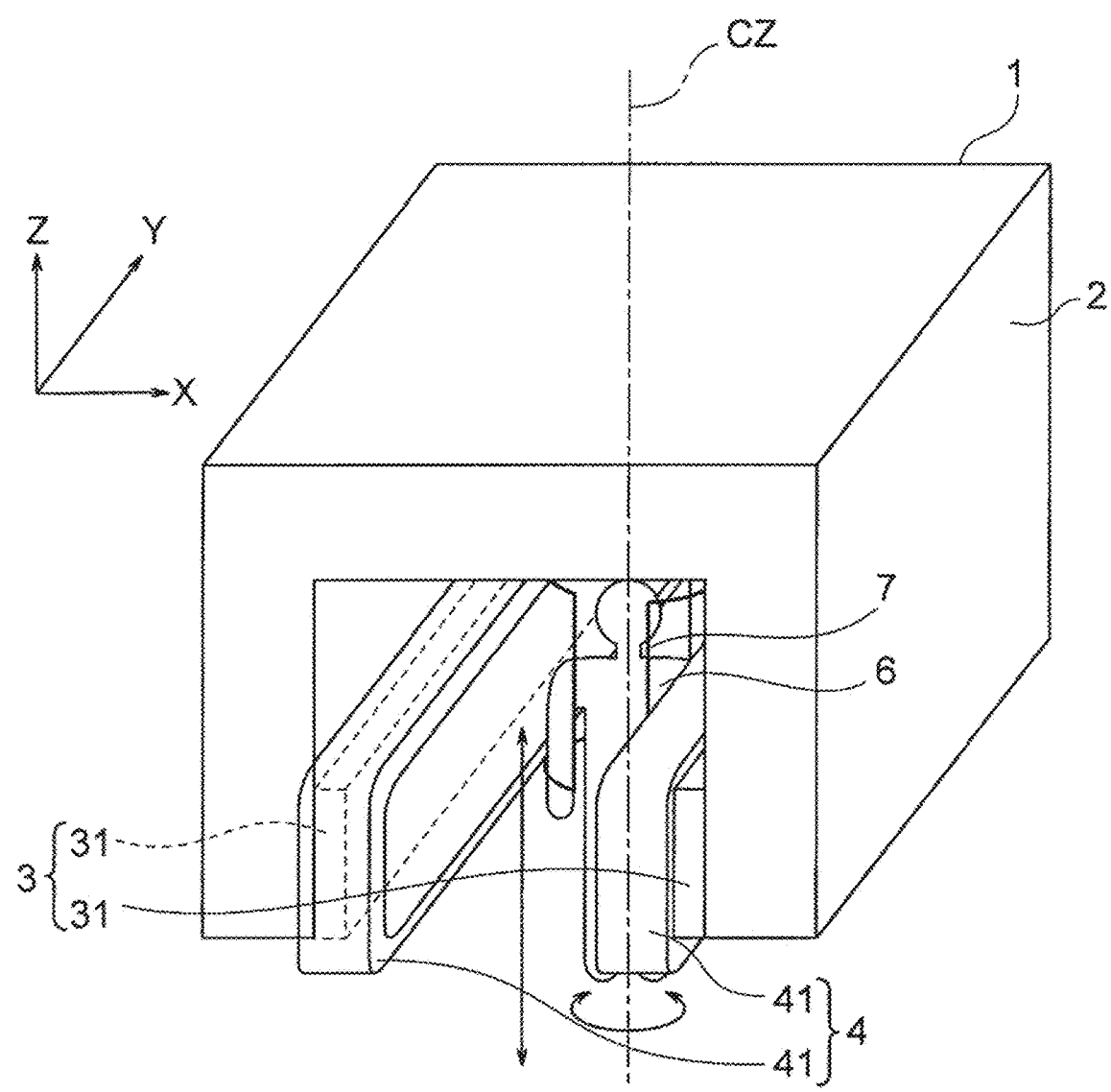
FIG. 28 is a schematic view for illustrating a configuration of an MPI apparatus including an electromagnetic device for MPI according to a fifth embodiment of the present invention.

FIG. 28 is a schematic view for illustrating a configuration of an MPI apparatus including the electromagnetic device 1 for MPI according to the fifth embodiment.

Here, in the first embodiment described above, in order to rotate the gradient magnetic field HX1 and the alternating magnetic field HX2 relative to the subject 6, the system in which the return yoke 2 is rotated with the center axis in the Z direction of the return yoke 2 being the rotation axis CZ is adopted. Further, in order to move the gradient magnetic field HX1 and the alternating magnetic field HX2 relative to the subject 6, the system in which the return yoke 2 is moved in the Z direction is adopted.

In contrast, in the fifth embodiment, in order to rotate the gradient magnetic field HX1 and the alternating magnetic field HX2 relative to the subject 6, a system in which the subject 6 is rotated with the body axis of the subject 6, which corresponds to the center axis in the Z direction of the return yoke 2, being the rotation axis CZ is adopted. Further, in order to move the gradient magnetic field HX1 and the alternating magnetic field HX2 relative to the subject 6, a system in which the subject 6 is moved in the Z direction is adopted.

Specifically, in order to rotate the subject 6, the rotation mechanism is configured to rotate a placement portion, on which the subject 6 is to be placed, with the rotation axis CZ being a rotation axis. Further, in order to move the subject 6, the movement mechanism is configured to move the placement portion, on which the subject 6 is to be placed, in the Z direction. When the subject 6 is a human body, the placement portion is, for example, a chair, on which the person can sit.

As described above, the rotation mechanism is configured to rotate the subject 6 with respect to the return yoke 2, which is stationary. Further, the movement mechanism is configured to move the subject 6 with respect to the return yoke 2, which is stationary.

As described above, according to the fifth embodiment, as opposed to the configurations in the first to fourth embodiments described above, the configuration in which the return yoke is held stationary, and in which the subject is rotated to rotate the gradient magnetic field and the alternating magnetic field relative to the subject is adopted. In this manner, the configuration in which the subject, which is lighter than the return yoke, is rotated instead of the return yoke is adopted, and hence an easier configuration of the electromagnetic device can be achieved.

REFERENCE SIGNS LIST

1 electromagnetic device for MPI, 2 return yoke, 20 yoke, 21 gradient magnetic field yoke, 22 alternating magnetic field yoke, 23 gradient magnetic field yoke, 23a base portion, 23b first protruding portion, 23c second protruding portion, 24 gradient magnetic field yoke, 24a first protruding portion, 24b second protruding portion, 25 gradient magnetic field yoke, 25a base portion, 25b first protruding portion, 25c second protruding portion, 25d third protruding portion, 26 gradient magnetic field yoke, 26a base portion, 26b first protruding portion, 26c second protruding portion, 26d third protruding portion, 27 upper gradient magnetic field yoke, 28 lower gradient magnetic field yoke, 3 gradient magnetic field generating unit, 31 permanent magnet, 32 gradient magnetic field generating coil, 33 power source, 34 upper gradient magnetic field generating coil, 35 lower gradient magnetic field generating coil, 4 alternating magnetic field generating unit, 41 alternating magnetic field generating coil, 42 alternating magnetic field generating coil, 43 power source, 44 alternating magnetic field generating coil, 5 motor, 6 subject, 7 receiving coil, 8 gradient/alternating magnetic field generating unit, 81 gradient/alternating magnetic field generating coil, 82 power source, 83 power source

The invention claimed is:

1. An electromagnetic device for magnetic particle imaging, comprising:
    a return yoke having a gap, which extends in a Y direction and forms a magnetic field space, where a width direction of the magnetic field space is defined as an X direction, and a length direction of the magnetic field space is defined as the Y direction;
    a gradient magnetic field generator, which is in the return yoke, and is configured to generate, in the magnetic field space, a gradient magnetic field in the X direction, and to form, in the magnetic field space, a zero-field region extending in the Y direction;
    an alternating magnetic field generator, which is in the return yoke, and is configured to generate an alternating magnetic field in the magnetic field space; and
    a rotator configured to rotate the gradient magnetic field and the alternating magnetic field relative to a subject with a Z direction being a rotation axis, where a direction perpendicular to the X direction and the Y direction is defined as the Z direction,
    wherein the return yoke includes:
        an alternating magnetic field yoke, which corresponds to the alternating magnetic field, and extends in the Y direction; and
        a pair of gradient magnetic field yokes that correspond to the gradient magnetic field, which are on an inside of the alternating magnetic field yoke, and which extend in the Y direction opposed to each other.

2. The electromagnetic device for magnetic particle imaging according to claim 1, further comprising a movement mechanism configured to move the gradient magnetic field and the alternating magnetic field in the Z direction relative to the subject.

3. The electromagnetic device for magnetic particle imaging according to claim 2,
    wherein the rotator is configured to rotate the return yoke, and
    wherein the movement mechanism is configured to move the return yoke.

4. The electromagnetic device for magnetic particle imaging according to claim 2,
    wherein the rotator is configured to rotate the subject, and
    wherein the movement mechanism is configured to move the subject.

5. The electromagnetic device for magnetic particle imaging according to claim 1,
    wherein the alternating magnetic field generator includes a pair of alternating magnetic field generating coils, which are on the inside of the alternating magnetic field yoke, and which extend in the Y direction opposed to each other, and
    wherein the gradient magnetic field generator includes a pair of permanent magnets, which are on the inside of the alternating magnetic field yoke, and which extend in the Y direction opposed to each other.

6. The electromagnetic device for magnetic particle imaging according to claim 5, wherein the pair of permanent magnets are individually on the pair of gradient magnetic field yokes.

7. The electromagnetic device for magnetic particle imaging according to claim 5,
    wherein each gradient magnetic field yoke of the pair of gradient magnetic field yokes includes:
        a base portion extending in the Y direction;
        a first protruding portion protruding in the X direction from one end of the base portion; and
        a second protruding portion protruding in the X direction from another end of the base portion, and
    wherein the pair of permanent magnets are individually on the base portions of the pair of gradient magnetic field yokes.

8. The electromagnetic device for magnetic particle imaging according to claim 5,
    wherein each gradient magnetic field yoke of the pair of gradient magnetic field yokes includes:
        a first protruding portion protruding in the X direction from the inside of the alternating magnetic field yoke; and
        a second protruding portion protruding in the X direction from the inside of the alternating magnetic field yoke and separated in the Z direction from the first protruding portion, and
    wherein the pair of permanent magnets are individually on inner side surfaces of the alternating magnetic field yoke, which are opposed to each other, between the first protruding portion and the second protruding portion of each gradient magnetic field yoke of the pair of gradient magnetic field yokes.

9. The electromagnetic device for magnetic particle imaging according to claim 1, further comprising, instead of the gradient magnetic field generator and the alternating magnetic field generator, a gradient/alternating magnetic field generator configured to generate the gradient magnetic field and the alternating magnetic field in the magnetic field space,
    wherein the gradient/alternating magnetic field generator includes a pair of gradient/alternating magnetic field generating coils, which are on the inside of the alternating magnetic field yoke, and which extend in the Y direction to be opposed to each other,
    wherein each gradient magnetic field yoke of the pair of gradient magnetic field yokes includes:
        a base portion extending in the Y direction;
        a first protruding portion protruding in the X direction from one end of the base portion;
        a second protruding portion protruding in the X direction from another end of the base portion; and
        a third protruding portion protruding in the X direction from a center portion of the base portion, and wherein the pair of gradient/alternating magnetic field generating coils are individually in the third protruding portions of the pair of gradient magnetic field yokes.

10. The electromagnetic device for magnetic particle imaging according to claim 1,
wherein the alternating magnetic field generator includes a pair of alternating magnetic field generating coils, which are on the inside of the alternating magnetic field yoke, and which extend in the Y direction opposed to each other,
wherein the gradient magnetic field generator includes a pair of gradient magnetic field generating coils, which are on the inside of the alternating magnetic field yoke, and which extend in the Y direction opposed to each other,
wherein each gradient magnetic field yoke of the pair of gradient magnetic field yokes includes:
a base portion extending in the Y direction;
a first protruding portion protruding in the X direction from one end of the base portion;
a second protruding portion protruding in the X direction from another end of the base portion; and
a third protruding portion protruding in the X direction from a center portion of the base portion, and
wherein the pair of gradient magnetic field generating coils are individually in the third protruding portions of the pair of gradient magnetic field yokes.

11. The electromagnetic device for magnetic particle imaging according to claim 1,
wherein the pair of gradient magnetic yokes of the return yoke include:
an upper gradient magnetic field yoke provided to correspond that corresponds to the gradient magnetic field, which is on the inside of the alternating magnetic field yoke, and which extends in the Y direction; and
a pair of lower gradient magnetic field yokes that correspond to the gradient magnetic field, which are on the inside of the alternating magnetic field yoke and on a lower side of the upper gradient magnetic field yoke, and which extend in the Y direction opposed to each other,
wherein the alternating magnetic field generator includes a pair of alternating magnetic field generating coils, which are on the inside of the alternating magnetic field yoke, and which extend in the Y direction opposed to each other, and
wherein the gradient magnetic field generator includes:
an upper gradient magnetic field generating coil, which is on the inside of the alternating magnetic field yoke, and which extends in the Y direction; and
a lower gradient magnetic field generating coil, which is on an outside of the alternating magnetic field yoke and on a lower side of the upper gradient magnetic field generating coil, and which extends in the Y direction.

12. The electromagnetic device for magnetic particle imaging according to claim 11, wherein the lower gradient magnetic field generating coil has an inner width that is wider than a gap width between the pair of lower gradient magnetic field yokes.

13. A magnetic particle imaging apparatus, comprising the electromagnetic device for magnetic particle imaging of claim 1.

14. An electromagnetic device for magnetic particle imaging, comprising:
a return yoke having a gap, which extends in a Y direction and forms a magnetic field space, where a width direction of the magnetic field space is defined as an X direction, and a length direction of the magnetic field space is defined as the Y direction;
a gradient magnetic field generator, which is in the return yoke, and is configured to generate, in the magnetic field space, a gradient magnetic field in the X direction, and to form, in the magnetic field space, a zero-field region extending in the Y direction;
an alternating magnetic field generator, which is in the return yoke, and is configured to generate an alternating magnetic field in the magnetic field space; and
a rotator configured to rotate the gradient magnetic field and the alternating magnetic field relative to a subject with a Z direction being a rotation axis, where a direction perpendicular to the X direction and the Y direction is defined as the Z direction,
wherein the return yoke includes:
an alternating magnetic field yoke, which corresponds to the alternating magnetic field, and which extends in the Y direction;
an upper gradient magnetic field yoke that corresponds to the gradient magnetic field, which is on the inside of the alternating magnetic field yoke, and which extends in the Y direction; and
a pair of lower gradient magnetic field yokes that correspond to the gradient magnetic field, which are on the inside of the alternating magnetic field yoke and on a lower side of the upper gradient magnetic field yoke, and which extend in the Y direction opposed to each other,
wherein the alternating magnetic field generator includes a pair of alternating magnetic field generating coils, which are on the inside of the alternating magnetic field yoke, and which extend in the Y direction opposed to each other, and
wherein the gradient magnetic field generator includes:
an upper gradient magnetic field generating coil, which is on the inside of the alternating magnetic field yoke, and which extends in the Y direction; and
a lower gradient magnetic field generating coil, which is on an outside of the alternating magnetic field yoke and on a lower side of the upper gradient magnetic field generating coil, and which extends in the Y direction.

15. The electromagnetic device for magnetic particle imaging according to claim 14, wherein the lower gradient magnetic field generating coil has an inner width that is wider than a gap width between the pair of lower gradient magnetic field yokes.

16. A magnetic particle imaging apparatus, comprising the electromagnetic device for magnetic particle imaging of claim 14.

* * * * *